(12) United States Patent
Kinstler et al.

(10) Patent No.: US 7,262,166 B2
(45) Date of Patent: *Aug. 28, 2007

(54) CHEMICALLY MODIFIED NOVEL ERYTHROPOIETIN STIMULATING PROTEIN COMPOSITIONS AND METHODS

(75) Inventors: Olaf Kinstler, Newbury Park, CA (US); Colin Gegg, Newbury Park, CA (US); Aimee Freeman, Newbury Park, CA (US); Thomas Boone, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/409,807

(22) Filed: Apr. 7, 2003

(65) Prior Publication Data

US 2003/0166566 A1   Sep. 4, 2003

Related U.S. Application Data

(63) Continuation of application No. 09/545,335, filed on Apr. 7, 2000, now Pat. No. 6,586,398.

(51) Int. Cl.
*A61K 38/00* (2006.01)
*A61K 38/18* (2006.01)
*C07K 17/00* (2006.01)

(52) U.S. Cl. .................. 514/12; 514/2; 514/8; 530/324; 530/350; 530/395; 530/397; 530/399; 530/402; 435/69.4

(58) Field of Classification Search .................. 514/12, 514/2, 8; 530/324, 350, 395, 397, 399, 402; 435/69.4
See application file for complete search history.

(56) References Cited

U.S. PATENT DOCUMENTS

| 4,002,531 | A |  | 1/1977 | Royer |  |
| 4,179,337 | A |  | 12/1979 | Davis et al. |  |
| 4,904,584 | A |  | 2/1990 | Shaw |  |
| 5,252,714 | A |  | 10/1993 | Harris et al. |  |
| 5,641,663 | A | * | 6/1997 | Garvin et al. | 435/320.1 |
| 5,824,784 | A |  | 10/1998 | Kinstler et al. |  |
| 5,834,594 | A |  | 11/1998 | Hakimi et al. |  |
| 5,985,265 | A |  | 11/1999 | Kinstler et al. |  |
| 6,340,742 | B1 |  | 1/2002 | Burg et al. |  |
| 6,583,272 | B1 |  | 6/2003 | Bailon |  |
| 6,586,398 | B1 | * | 7/2003 | Kinstler et al. | 514/12 |

FOREIGN PATENT DOCUMENTS

| CA | 2204640 |  | 1/2001 |
| WO | WO95/05465 | * | 2/1995 |
| WO | WO98/05363 | * | 2/1998 |

OTHER PUBLICATIONS

Delagado etal., Critical Reviews in Therapeutic Drug Carrier Systems, vol. 9, No. 3,4, pp. 249-304, 1992.*
MacDougall, et al., "Comparison of the Pharmacokinetics of Novel Erythropoiesis Stimulating Protein (NESP) and Epoetin Alfa (rhEPO) in Dialysis Patients", *Journal of the American Society of Nephrology*, vol. 8, pp. 268A, (1997).
Egrie, et al., "Novel Erythropoiesis Stimulating Protein (NESP) has a longer Serum Half-life and greater *in vivo* Biological Activity Than Recombinant Human Erythropoietin (rHuEPO)", *Blood*, vol. 90, pp. 56a, (1997).
MacDougall et al., J. Am. Soc. Nephrol., "*Pharmacokinetics of Novel Erythropoiesis Stimulating Protein Compared with Epoetin Alfa in Dialysis Patients*" 10, 2392-2395 (1999).
Nandini V. Katre, Advanced Drug Delivery Reviews, "*The Conjugation of Proteins with Polyethylene Glycol and other Polymers, Altering Properties of Proteins to Enhance Their Therapeutic Potential*" 10, 91-114 (1993).
Nucci, et al., Advanced Drug Delivery Reviews, "*The Therapeutic Value of Poly(ethylene glycol)-modified Proteins*" 133-151 (1991).

* cited by examiner

*Primary Examiner*—Jon Weber
*Assistant Examiner*—Abdel A. Mohamed
(74) *Attorney, Agent, or Firm*—Petrina S. Hsi

(57) ABSTRACT

The present invention broadly relates to the field of protein modification, and, more specifically, the attachment of water soluble polymers to novel erythropoietin stimulating protein (NESP).

16 Claims, 22 Drawing Sheets

PEG Size

PEG Conformation

Degree of Substitution

Reductive Alkylation:

Acylation:

Hydrazone Reduction:

Days after NESP treatment

20kD monoPEG-NESP

30kD monoPEG-NESP

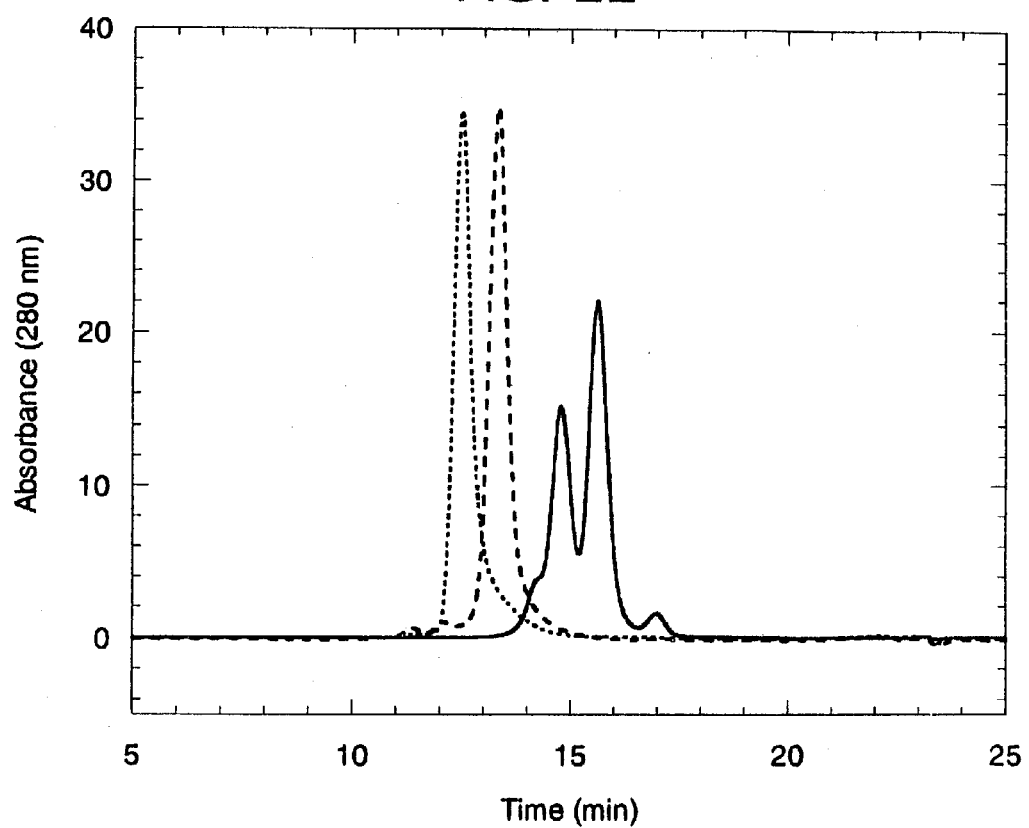

SEQUENCE LISTING

```
<160> NUMBER OF SEQ ID NOS: 1

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Asn Glu Thr
                 20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
         50                  55                  60

Gln Gly Leu Ala Leu Leu Ser Glu Ala Val Leu Arg Gly Gln Ala Leu
 65                  70                  75                  80

Leu Val Asn Ser Ser Gln Val Asn Glu Thr Leu Gln Leu His Val Asp
                 85                  90                  95

Lys Ala Val Ser Gly Leu Arg Ser Leu Thr Thr Leu Leu Arg Ala Leu
             100                 105                 110

Gly Ala Gln Lys Glu Ala Ile Ser Pro Pro Asp Ala Ala Ser Ala Ala
         115                 120                 125

Pro Leu Arg Thr Ile Thr Ala Asp Thr Phe Arg Lys Leu Phe Arg Val
     130                 135                 140

Tyr Ser Asn Phe Leu Arg Gly Lys Leu Lys Leu Tyr Thr Gly Glu Ala
145                 150                 155                 160

Cys Arg Thr Gly Asp
                165
```

CHEMICALLY MODIFIED NOVEL ERYTHROPOIETIN STIMULATING PROTEIN COMPOSITIONS AND METHODS

This application is a continuation of application Ser. No. 09/545,335 filed on Apr. 7, 2000, now U.S. Pat. No. 6,586, 398, which is hereby incorporation by reference.

BACKGROUND OF THE INVENTION

Novel erythropoietin stimulating-protein (NESP) is a hyperglycosylated erythropoietin analog having five changes in the amino acid sequence of rHuEPO which provide for two additional carbohydrate chains. More specifically, NESP contains two additional N-linked carbohydrate chains at amino acid residues 30 and 88 (numbering corresponding to the sequence of human EPO)(see PCT Application No. US94/02957, herein incorporated by reference in its entirety). NESP is biochemically distinct from EPO, having a longer serum half-life and higher in vivo biological activity; Egrie et al., ASH 97, Blood, 90:56a (1997). NESP has been shown to have ~3 fold increase in serum half-life in mice, rats, dogs and man; Id. In mice, the longer serum half-life and higher in vivo activity allow for less frequent dosing (once weekly or once every other week) compared to rHuEPO to obtain the same biological response; Id.

A pharmacokinetic study demonstrated that, consistent with the animal studies, NESP has a significantly longer serum half-life than rHuEPO in chronic renal failure patients, suggesting that a less frequent dosing schedule may also be employed in humans; MacDougall, et al., *J American Society of Nephrology*, 8:268A (1997). A less frequent dosing schedule would be more convenient to both physicians and patients, and would be particularly helpful to those patients involved in self-administration. Other advantages to less frequent dosing may include less drug being introduced into patients, a reduction in the nature or severity of the few side-effects seen with rHuEPO administration, and increased compliance.

Although the extended half-life of NESP offers the advantage of less frequent dosing relative to EPO, there are still potential indications, such as chemotherapy, which may require an even longer therapeutic half-life than NESP currently demonstrates.

A common approach often used to extend the half-lives of proteins in vivo is the chemical conjugation of a water soluble polymer, such as polyethylene glycol (PEG), to the protein of interest. Generally, polyethylene glycol molecules are connected to the protein via a reactive group found on the protein. Amino groups, such as those on lysine residues or at the N-terminus, are convenient for such attachment.

A variety of approaches have been used to attach the polyethylene glycol molecules to the protein (PEGylation). For example, Royer (U.S. Pat. No. 4,002,531) states that reductive alkylation was used for attachment of polyethylene glycol molecules to an enzyme. Davis et al. (U.S. Pat. No. 4,179,337) disclose PEG:protein conjugates involving, for example, enzymes and insulin. Shaw (U.S. Pat. No. 4,904,584) disclose the modification of the number of lysine residues in proteins for the attachment of polyethylene glycol molecules via reactive amine groups. Hakimi et al. (U.S. Pat. No. 5,834,594) disclose substantially non-immunogenic water soluble PEG:protein conjugates, involving for example, the proteins IL-2, interferon alpha, and IL-1ra. The methods of Hakimi et al. involve the utilization of unique linkers to connect the various free amino groups in the protein to PEG. Kinstler et al. (U.S. Pat. Nos. 5,824,784 and 5,985,265) teach methods allowing for selectively N-terminally chemically modified proteins and analogs thereof, including G-CSF and consensus interferon. Importantly, these modified proteins have advantages as relates to protein stability, as well as providing for processing advantages.

PEGylation approaches such as those described above are traditionally applied to non-glycosylated proteins derived from bacterial expression systems in order to render improvements in solubility and in vivo circulating half-lives (such properties are typically conferred to glycosylated proteins (glycoproteins) through the carbohydrate moieties added in the course of eukaryotic expression). The effects of PEGylation on the in vivo half-lives of non-glycosylated proteins is generally thought to derive from the physico-chemical and dynamic properties of PEG conferring a larger hydrodynamic volume and total mass to the conjugate, thus reducing the rate of renal clearance. Additional benefits typically include increased solubility and decreased immunogenicity for the conjugate. However, not all proteins respond equally to PEGylation and there is no guarantee of improved performance.

The present invention is based upon the surprising finding that a highly glycosylated protein, e.g., NESP, can be PEGylated to provide a pharmaceutical composition with an even more dramatic sustained duration profile than NESP, allowing for a once every 4–6 week dosing for raising hematocrit and treating anemia, and thus providing tremendous therapeutic advantage.

SUMMARY OF THE INVENTION

The present invention relates to a substantially homogenous preparation of chemically modified NESP (or analog thereof) and related methods.

The present invention further relates to a substantially homogenous preparation of N-terminally chemically modified NESP (or analog thereof).

The present invention further relates to a preparation of chemically modified NESP represented as a mixed population of either monosubstituted positional isoforms or polysubstituted forms.

BRIEF DESCRIPTION OF THE FIGURES

FIG. 22 depicts size exclusion HPLC chromatograms of the 5 kD poly-PEG:NESP (-), the 20 kD mono-PEG:NESP (‾ ‾ ‾) and 30 kD mono-PEG:NESP (- - -). The SEC column was a Tosohaas TSK 3000 SW×1 (5 micron-7.8 mm×30 cm) which utilized 100 mM NaHPO$_4$, 10% ethanol, 150 mM NaCl, pH 6.9, to elute the products.

DETAILED DESCRIPTION OF THE INVENTION

To discover if the in vivo therapeutic half-life of a glycoprotein such as NESP would benefit from PEGylation, a variety of different PEG:NESP conjugates were synthesized and tested in vivo for prolonged erythropoiesis.

Figure 1A:
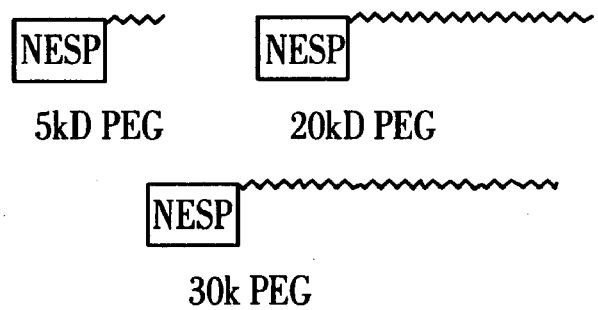
FIG. 1 depicts the design strategy for NESP PEGylation: (A) PEG polymer size is varied from 5 kD, 20 kD and 30 kD; (B) PEG polymer conformation can be either linear or branched with total molecular weights of 10 kD, 20 kD or 40 kD PEG; and (C) preparations of PEG:NESP with different degrees of substitution can be isolated to include: mono-PEG, di-PEG or, in some cases, tri-PEG NESP.
Figure 1B:
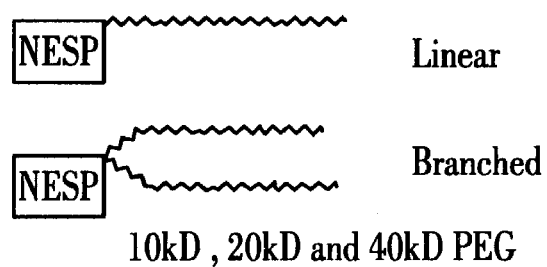
Figure 1C:

In order to both optimize the potential effects of PEGylation and to identify the preferred sites and chemistries of PEG attachment, a design strategy was employed wherein polymer length, conformation, and both the degree and sites of attachment were varied (see FIG. 1).

Figure 2A:
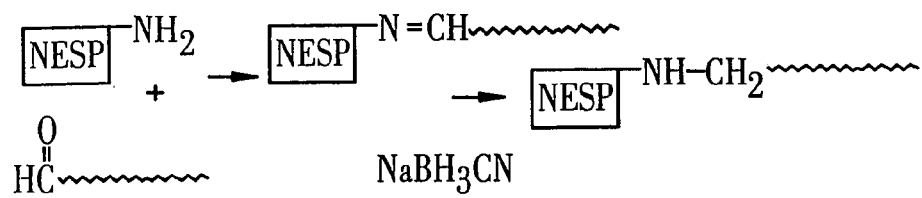
FIG. 2 depicts the various reaction chemistries for PEGylation of NESP: (A) reductive alkylation of NESP with PEG-aldehyde; (B) acylation of NESP with N-succinimidyl ester of PEG; and (C) PEGylation of the NESP polysaccharide side chains by limited periodate oxidation of the carbohydrate with the resultant aldehyde reacted with PEG-hydrazide to form a hydrazone linkage followed by subsequent reduction with sodium cyanoborohydride to stabilize the linkage.
Figure 2B:
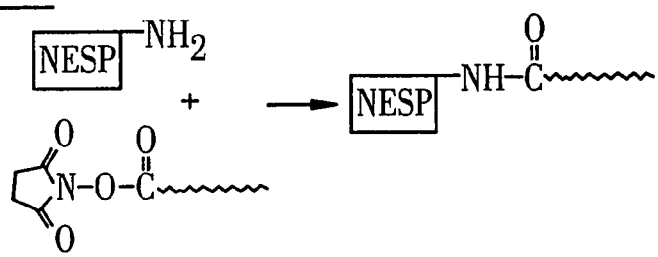
Figure 2C:
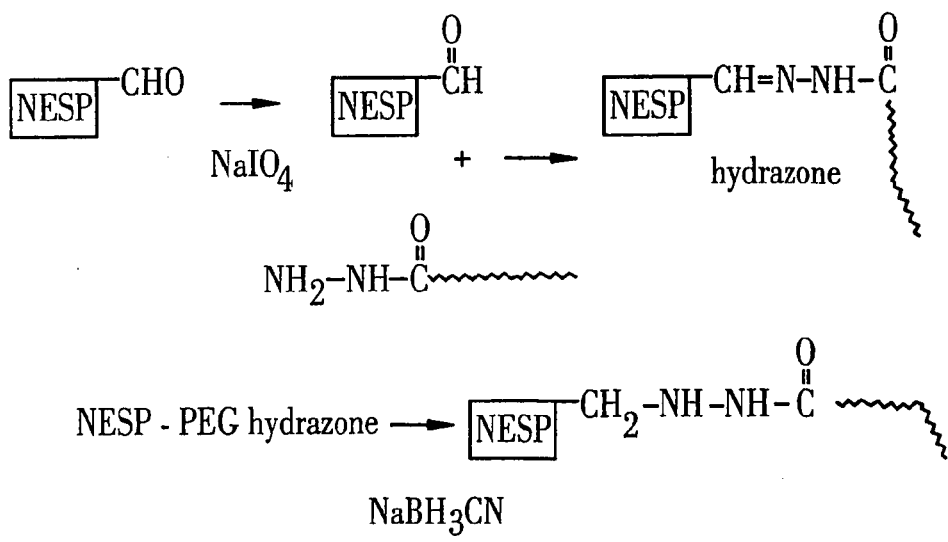
Figure 3:
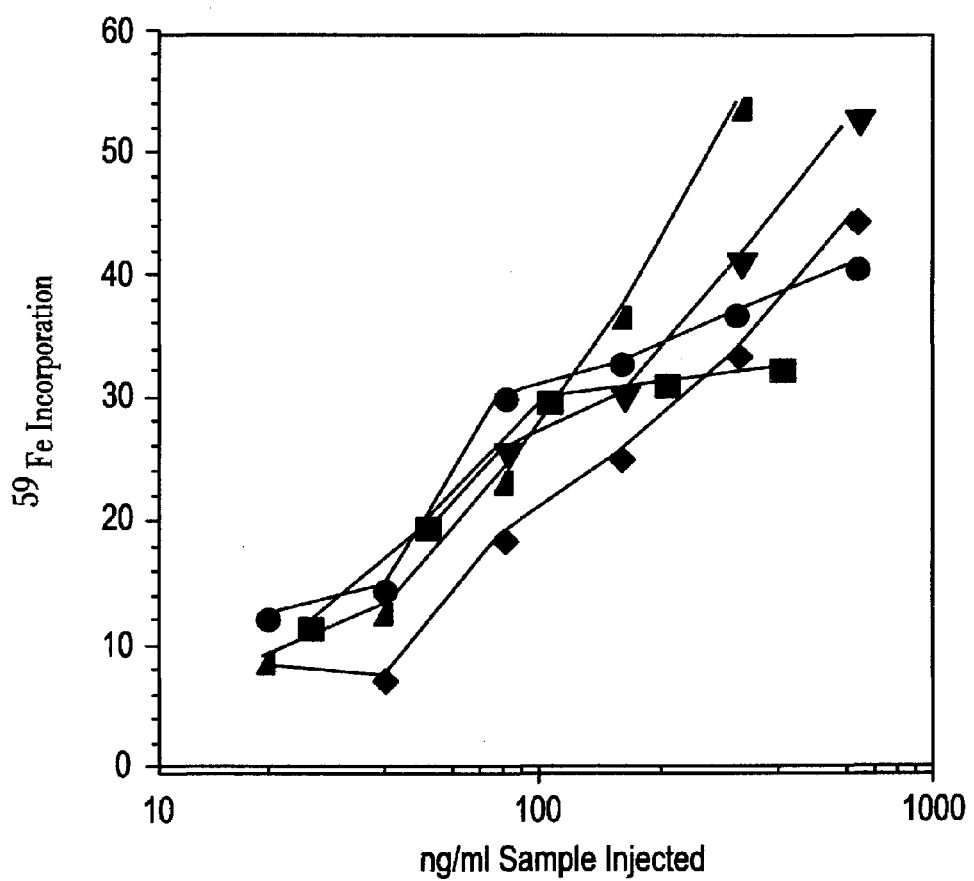
FIG. 3 is a graph depicting in vivo activity data of various 5 kD poly-PEG:NESP conjugates vs. unmodified NESP (■). Samples -▲-, -▼-, -●-, and -◆- are mixtures of 5 kD poly-PEG:NESP with progressively lower degrees of substitution. % iron uptake is plotted vs. ng/mL administered.
Figure 4:
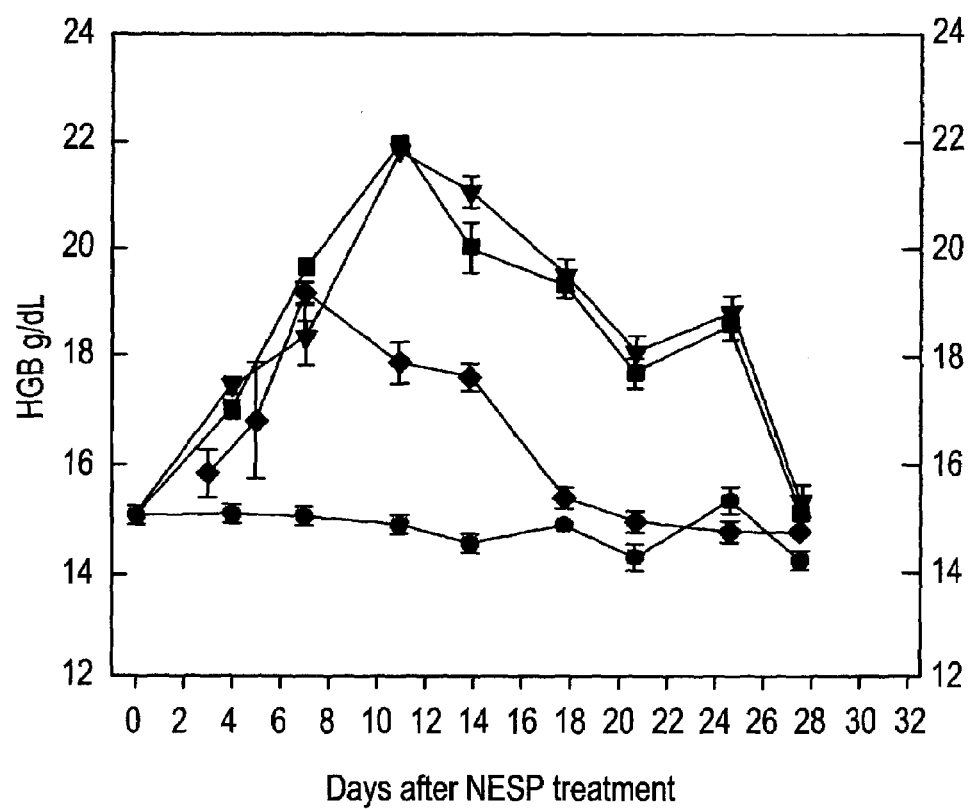
FIG. 4 is a graph depicting prolongation of elevated hemoglobin (HGB) levels in response to treatment with various PEG:NESP conjugates relative to unmodified NESP. Single bolus injection of 100 μg/kg NESP (♦), 20 kD linear mono-PEG:NESP conjugate derived from NHS-ester activated methoxy-PEG (■), 20 kD linear (~80% mono-PEG:NESP and 20% di-PEG:NESP) conjugate derived by reductive alkylation from aldehyde activated PEG (▼), and a saline control (●). HGB (g/dL) is plotted vs. # days post-treatment.

Methods for preparing the PEGylated NESP of the present invention generally comprise the steps of (a) reacting NESP with polyethylene glycol (such as a reactive ester or aldehyde derivative of PEG) under conditions whereby NESP becomes attached to one or more PEG groups, and (b) obtaining the reaction product(s). Because the specific sites of NESP modification might significantly alter the intrinsic activity of the conjugate, three different PEGylation chemistries were explored (see FIG. 2). The first approach utilizes reductive alkylation to conjugate a PEG-aldehyde (O-(3-Oxopropyl)-O'-methylpolyethylene glycol) to a primary amine of NESP. Under appropriate conditions, this approach has been demonstrated to yield PEG conjugates predominately modified through the α-amine at the protein N-terminus. Because the PEG is linked through a secondary amine by reductive alkylation there is the potential to preserve the charge at the protein N-terminus.

The second chemistry applied to PEGylation of NESP was the acylation of the primary amines of NESP using the NHS-ester of methoxy-PEG (O-[(N-Succinimidyloxycarbonyl)-methyl]-O'-methylpolyethylene glycol). In contrast to the previous chemistry, acylation with methoxy PEG-NHS results in an amide linkage which will eliminate the charge from the original primary amine.

The final attachment chemistry evaluated utilized a mild oxidation of NESP under conditions selected to target the pendant diol of the penultimate glycosyl unit sialic acid for oxidation to an aldehyde. The resultant glycoaldehyde was then reacted with a methoxy-PEG-hydrazide (O-(Hydrazinocarbonylmethyl)-O'-methylpolyethylene glycol) to form a semi-stable hydrazone between the PEG and NESP. The hydrazone was subsequently reduced by sodium cyanoborohydride to produce a stable PEG:NESP conjugate.

The present methods each provide for a substantially homogenous mixture of polymer:protein conjugate. "Substantially homogenous" as used herein means that only polymer:protein conjugate molecules are observed. As ascertained by peptide mapping and N-terminal sequencing, one example below provides for a preparation which is at least 90% polymer:protein conjugate, and at most 10% unreacted protein. Preferably, the PEGylated material is at least 95% of the preparation (as in the working example below) and most preferably, the PEGylated material is 99% of the preparation or more. The polymer:protein conjugate has biological activity and the present "substantially homogenous" PEGylated NESP preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various protein with various numbers of polymer moieties attached (i.e., di-, tri-, tetra-, etc.) and combine said conjugates with the mono-polymer:protein conjugate prepared using the present methods, and have a mixture with a predetermined proportion of mono-polymer:protein conjugate.

Initial experiments designed to evaluate and optimize PEG:protein reaction stoichiometries revealed that PEGylation by reductive alkylation using PEG-aldehyde was surprisingly somewhat inefficient, requiring substantially higher molar ratios of PEG to protein than typically observed with non-glycosylated proteins. Similarly, acylation with PEG-NHS esters was also slower and less efficient than expected. It was thus evident that the PEGylation of non-glycosylated proteins was not necessarily predictive of the PEGylation of glycosylated proteins and that further optimization of reaction conditions was necessary.

The polymer molecules contemplated for use in the PEGylation approaches described herein may be selected from among water soluble polymers or a mixture thereof. The water soluble polymer may be selected from the group consisting of, for example, polyethylene glycol, monomethoxy-polyethylene glycol, dextran, poly-(N-vinyl pyrrolidone), propylene glycol homopolymers, a polypropylene oxide/ethylene oxide co-polymer, polyoxyethylated polyols (e.g., glycerol), dextran, HPMA, Fleximer™, and polyvinyl alcohol. The polymer selected should be water soluble so that the protein to which it is attached does not precipitate in an aqueous environment, such as a physiological environment. For the acylation reactions, the polymer(s) selected should have a single reactive ester group. For the present reductive alkylation, the polymer(s) selected should have a single reactive aldehyde group. A preferred reactive PEG-aldehyde is polyethylene glycol propionaldehyde, which is water stable, or mono C1–C10 alkoxy or aryloxy derivatives thereof (see, U.S. Pat. No. 5,252,714). The polymer may be branched or unbranched. Preferably, for therapeutic use of the end-product preparation, the polymer will be pharmaceutically acceptable.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy- or aryloxy-polyethylene glycol.

The proportion of polyethylene glycol molecules to protein molecules will vary, as will their concentrations in the reaction mixture. In general, the optimum ratio (in terms of efficiency of reaction in that there is no excess unreacted protein or polymer) will be determined by the molecular weight of the polyethylene glycol selected and on the number of available reactive groups (typically ∝or -)-amino groups) available. As relates to molecular weight, the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio. In the present invention, several different linear PEG polymer lengths were evaluated (5 kD, 20 kD and 30 kD). Similarly, conjugates of two-armed branched PEG polymers (10 kD, 20 kD and 40 kD) were also tested. From each preparation, samples of mono-substituted and di-substituted PEG:NESP were isolated to investigate the effects of secondary sites of PEGylation.

In general, for the PEGylation reactions contemplated herein, the preferred average molecular weight is about 2 kDa to about 100 kDa (the term "about" indicating ±1 kDa). More preferably, the average molecular weight is about 5 kDa to about 40 kDa. The ratio of water-soluble polymer to NESP will generally range from 1:1 for monoPEG-, 2:1 for diPEG etc, and the mass ratios for PEG:protein would run ~1:7 for 5 kD mono-PEG to ~1:1.3 for 30 kD monoPEG.

The method of obtaining the PEGylated NESP preparation may be by purification of the PEGylated material from a population of non-PEGylated NESP molecules. For example, presented below is an example where mono- and/or di-PEGylated NESP is separated using ion exchange size chromatography. Size exclusion chromatography is used as an analytical tool to Characterize the purified products.

The present invention also provides a method for selectively obtaining N-terminally chemically modified NESP. The method comprises reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. The reaction is performed at pH which allows one to take advantage of the $pK_a$ differences between the $\epsilon$-amino groups of the lysine residues and that of the $\alpha$-amino group of the N-terminal residue of the protein. By such selective derivatization attachment of a water soluble polymer to a protein is controlled: the conjugation with the polymer takes place predominantly at the N-terminus of the protein and no significant modification of other reactive groups, such as the lysine side chain amino groups, occurs. The preparation will preferably be greater than 80% mono-polymer:protein conjugate, and more preferably greater than 95% mono-polymer:protein conjugate.

NESP of the present invention is a hyperglycosylated EPO analog comprising two additional glycosylation sites with an additional carbohydrate chain attached to each site. NESP was constructed using site-directed mutagenesis and expressed in mammalian host cells. Details of the production of NESP are provided in co-owned PCT Application No. US94/02957. New N-linked glycosylation sites for rHuEPO were introduced by alterations in the DNA sequence to encode the amino acids Asn-X-Ser/Thr in the polypeptide chain. DNA encoding NESP was transfected into Chinese Hamster Ovary (CHO) host cells and the expressed polypeptide was analyzed for the presence of additional carbohydrate chains. In a preferred embodiment, NESP will have two additional N-linked carbohydrate chains at residues 30 and 88. The numbering of the amino acid sequence is that of human erythropoietin (EPO). The amino acid sequence of NESP is that depicted in SEQ ID NO: 1. It is understood that NESP will have the normal complement of N-linked and O-linked glycosylation sites in addition to the new sites.

The NESP of the present invention may also include conservative amino acid changes at one or more residues in SEQ ID NO: 1. These changes do not result in addition of a carbohydrate chain and will have little effect on the biological activity of the analog.

In general, comprehended by the present invention are pharmaceutical compositions comprising effective amounts of protein or derivative products of the invention together with pharmaceutically acceptable diluents, stabilizers, preservatives, solubilizers, emulsifiers, adjuvants and/or carriers. Such compositions include diluents of various buffer content (e.g., Tris-HCl, phosphate), pH and ionic strength; additives such as detergents and solubilizing agents (e.g., Polysorbate 20, Polysorbate 80), anti-oxidants (e.g., ascorbic acid, sodium metabisulfite), preservatives (e.g., Thimerosol, benzyl alcohol) and bulking substances (e.g., lactose, mannitol); see, e.g., Remington's Pharmaceutical Sciences, 18th Ed. (1990, Mack Publishing Co., Easton, Pa. 18042) pages 1435:1712 which are herein incorporated by reference. An effective amount of active ingredient is a therapeutically, prophylactically, or diagnostically effective amount, which can be readily determined by a person skilled in the art by taking into consideration such factors as body weight, age, and therapeutic or prophylactic goal.

The PEG:NESP compositions of the present invention may also include a buffering agent to maintain the pH of the solution within a desired range. Preferred agents include sodium acetate, sodium phosphate, and sodium citrate. Mixtures of these buffering agents may also be used. The amount of buffering agent useful in the composition depends largely on the particular buffer used and the pH of the solution. For example, acetate is a more efficient buffer at pH 5 than pH 6 so less acetate may be used in a solution at pH 5 than at pH 6. The preferred pH range for the compositions of the present invention is pH 3.0–7.5.

The compositions of the present invention may further include an isotonicity adjusting agent to render the solution isotonic and more compatible for injection. The most preferred agent is sodium chloride within a concentration range of 0–150 mM.

As used herein, and when contemplating PEG:NESP conjugates, the term "therapeutically effective amount" refers to an amount which gives an increase in hematocrit that provides benefit to a patient. The amount will vary from one individual to another and will depend upon a number of factors, including the overall physical condition of the patient and the underlying cause of anemia. For example, a therapeutically effective amount of rHuEPO for a patient suffering from chronic renal failure is 50 to 150 units/kg three times per week. The amount of rHuEPO used for therapy gives an acceptable rate of hematocrit increase and maintains the hematocrit at a beneficial level (usually at least about 30% and typically in a range of 30% to 36%). A therapeutically effective amount of the present compositions may be readily ascertained by one skilled in the art using publicly available materials and procedures.

The invention provides for administering PEG:NESP conjugates less frequently than NESP and/or EPO. The dosing frequency will vary depending upon the condition being treated, but in general will be about one time per 4–6 weeks. It is understood that the dosing frequencies actually used may vary somewhat from the frequencies disclosed herein due to variations in responses by different individuals to the PEG:NESP conjugates; the term "about" is intended to reflect such variations.

The present invention may thus be used to stimulate red blood cell production and correct depressed red cell levels. Most commonly, red cell levels are decreased due to anemia. Among the conditions treatable by the present invention include anemia associated with a decline or loss of kidney function (chronic renal failure), anemia associated with myelosuppressive therapy, such as chemotherapeutic or antiviral drugs (such as AZT), anemia associated with the progression of non-myeloid cancers, and anemia associated with viral infections (such as HIV). Also treatable are conditions which may lead to anemia in an otherwise healthy individual, such as an anticipated loss of blood during surgery. In general, any condition treatable with rHuEPO and/or NESP may also be treated with the PEG:NESP conjugates of the invention.

The invention also provides for administration of a therapeutically effective amount of iron in order to maintain increased erythropoiesis during therapy. The amount to be given may be readily determined by one skilled in the art based upon therapy with rHuEPO.

PEG:NESP conjugates prepared in accordance with the present invention is preferably administered by injection intraperitoneally, subcutaneously, or intramuscularly. However, it would be clear to one skilled in the art that other routes of delivery could also be effectively utilized using the compositions of the present invention.

The following examples are offered to more fully illustrate the invention, but are not to be construed as limiting the scope thereof. Example 1 describes the preparation and testing of PEG:NESP conjugates prepared by coupling either 5 kD or 20 kD methoxy-PEG-hydrazides to NESP through aldehydes generated in the NESP carbohydrate chains by sodium petiodate oxidation. Example 2 describes the preparation and testing of PEG:NESP conjugates prepared utilizing 20 kD PEG polymers as NHS-PEG esters and PEG-aldehydes to produce PEG-NESP conjugates by acylation and reductive alkylation respectively. Example 3 demonstrates the effects on activity of the degree of substitution and variations of the polymer size and conformation for various PEG:NESP conjugates. Example 4 describes the efficacy of three PEG:NESP conjugates: 20 kD mono-PEG:NESP; the 5 kD poly-PEG:NESP mixture; and 30 kD mono-PEG:NESP, as examined at three different doses relative to a NESP control, in an anemic mouse model. In Example 5, three different PEG-NESP conjugates were evaluated in a normal mouse bioassay to compare and contrast their erythropoietic potential and duration.

EXAMPLE 1

PEG:NESP conjugates were produced by coupling either 5 kD or 20 kD methoxy-PEG-hydrazides to NESP through aldehydes generated in the NESP carbohydrate chains by sodium periodate oxidation. The degree of modification was controlled by varying the sodium periodate concentration during oxidation.

The conjugates were prepared by first oxidizing NESP (2–4 mg/ml in 50 mM sodium acetate) with either 1 mM or 10 mM sodium meta-periodate (Sigma) for thirty minutes at room temperature in 100 mM sodium acetate, pH 5.6. The periodate is then removed by buffer exchange into 100 mM sodium acetate, pH 5.4. Methoxy-PEG-hydrazide (Shearwater Polymers) is then added at 5–100 fold molar excess polymer:protein, with 100-fold excess preferred. The intermediate hydrazone linkage was further reduced by addition of 15 mM sodium cyanoborohydride (Sigma) and allowed to react overnight at 4° C. The resultant conjugates were then fractionated by size exclusion FPLC using a Superdex 75, 26 mm×60 dm column (Pharmacia) eluted with 20 mM sodium phosphate, 150 mM NaCl, pH 7.2. The resultant preparations ranged in size from ~40 kD to ~200 kD, as estimated by SDS-PAGE.

Samples of PEG:NESP were tested for receptor binding in an in vitro EIA format. The in vitro assay is a displacement assay wherein the PEG:NESP conjugates compete for binding of the EPO receptor with an EPO-HRP conjugate used as a reporter. The in vitro assay results suggest that the PEG:NESP conjugates had a lower apparent affinity for the NESP receptor.

Bioactivity of various PEG:NESP conjugates was then evaluated in vivo by monitoring iron uptake in rodents after a single subcutaneous dose of conjugate. In the assay, mice are preconditioned in a hyperbaric chamber to suppress expression of endogenous erythropoietin, then dosed with a single, subcutaneous bolus injection of NESP or a PEG:NESP conjugate. After five days, the mice receive an intravenous injection of $Fe^{59}$ isotope as a tracer to monitor iron uptake in the red blood cells. Two days after the administration of $Fe^{59}$, the animals are sacrificed and analyzed for iron uptake as a function of dose.

Initially, several pools of 5 kD poly-PEG:NESP conjugates with varying degrees of PEGylation were tested for iron uptake as a function of conjugate dose. The in vivo assay results are depicted in FIG. 3, and demonstrated that the PEG:NESP conjugates prepared by coupling PEG-hydrazide to oxidized NESP perform comparably to NESP alone in the iron uptake bioassay.

EXAMPLE 2

This example describes the preparation and testing of PEG:NESP conjugates prepared utilizing NHS-PEG esters and PEG-aldehydes produced from 20 kD PEG polymers. Reaction stoichiometries and buffer conditions were optimized for each chemistry to produce 20 kD mono-PEG:NESP conjugates in good yield. A 20 kD mono-PEG:NESP derived by acylation of NESP with the 20 kD methoxy-PEG-NHS ester was prepared, as well as a mixture (~80%/20%) of 20 kD mono/di-PEG:NESP derived by reductive alkylation of NESP with 20 kD methoxy-PEG-aldehyde.

The reaction with methoxy-PEG-aldehyde (Shearwater Polymers) can be carried but from pH 4–6 with the optimum being at pH 5.2. The concentration of NESP in the reaction mixture was 4 mg/ml in 50 mM sodium acetate. The molar excess of PEG aldehyde used was 5–20 fold, and sodium cyanoborohydride was added to a final 15 mM concentration. The reaction was stirred for 1 hour at ambient temperature and then for 18 hours at 5° C. Upon completion of the reaction, the mixture was diluted to a conductivity of less than 5 mS/cm, the pH raised to 7.0, and the mixture loaded onto a Q Sepharose HP column (Pharmacia). The products were eluted from the column utilizing a linear gradient from 50 mM NaCl to 200 mM NaCl buffered in 10 mM Bis-Tris-Propane, pH 7.0. This purification allows for separation of species based on the number of PEG molecules attached to NESP.

The reaction with PEG activated NHS ester, methoxy-SPA-PEG (Shearwater Polymers), was carried out at pH 8.0 at a NESP concentration from 2–4 mg/ml in 50 mM Bicine buffer. A buffered solution of NESP was added to 10–20 molar equivalents of PEG. The reaction was stirred for 1 hour at ambient temperature. Upon completion of the reaction, the mixture was diluted to a conductivity of less than 5 mS/cm, the pH raised to 7.0, and the sample loaded onto a QHP column (Pharmacia). The products were eluted with a linear gradient from 50 mM NaCl to 200 mM NaCl buffered in 10 mM Bis-Tris-Propane, pH 7.0.

The two isolated PEG:NESP conjugates, a 20 kD mono-PEG:NESP (NHS) and a mixture (~80%/20%) of 20 kD mono/di-PEG:NESP (aldehyde) were then tested in a murine in vivo bioassay. The murine bioassay measures reticulocytes, a red blood cell precursor, and hemoglobin as monitors of erythropoiesis in response to a single dose of NESP or PEG:NESP in normal mice. Specifically, the bioassay measures the intensity and duration of an increased hemoglobin and reticulocyte response resulting from subcutaneous bolus injections of 100 μg/kg in female BDF 1 mice. The assay results are depicted in FIG. 4, and the results of the study indicated a significant increase and prolongation of the hemoglobin response from the PEG:NESP conjugates relative to an equivalent dose of NESP alone.

EXAMPLE 3

This example demonstrates the effects on activity of the degree of substitution and variations of the polymer size and conformation for PEG:NESP conjugates.

Using both methoxy-PEG-aldehyde and methoxy-PEG-NHS based chemistries, a variety of PEG:NESP conjugates were synthesized from 5 kD, 20 kD and 30 kD linear polymers as well as 10 kD, 20 kD and 40 kD branched polymers. From these reactions, preparations of mono-substituted and di-substituted PEG:NESP were isolated chromatographically and tested for prolonged erythropoiesis in the mouse bioassay.

The reaction with methoxy-PEG-aldehyde (Shearwater Polymers) was run with a NESP concentration of 4 mg/ml and a 25-fold molar excess of PEG in 20 mM NaOAc, pH 5.0, with sodium cyanoborohydride added to a final concentration of 20 mM. The reaction was stirred overnight at 4° C., diluted 4-fold with 20 mM Tris, pH 7.2, and the pH adjusted to pH 7.4 with NaOH. The diluted reaction mixture was then loaded onto a 5 ml HiTrap Q Sepharose HP column (Pharmacia). The PEGylated NESP isoforms were resolved by elution with a O-150 mM NaCl gradient in 20 mM Tris, pH 7.2.

Figure 5:
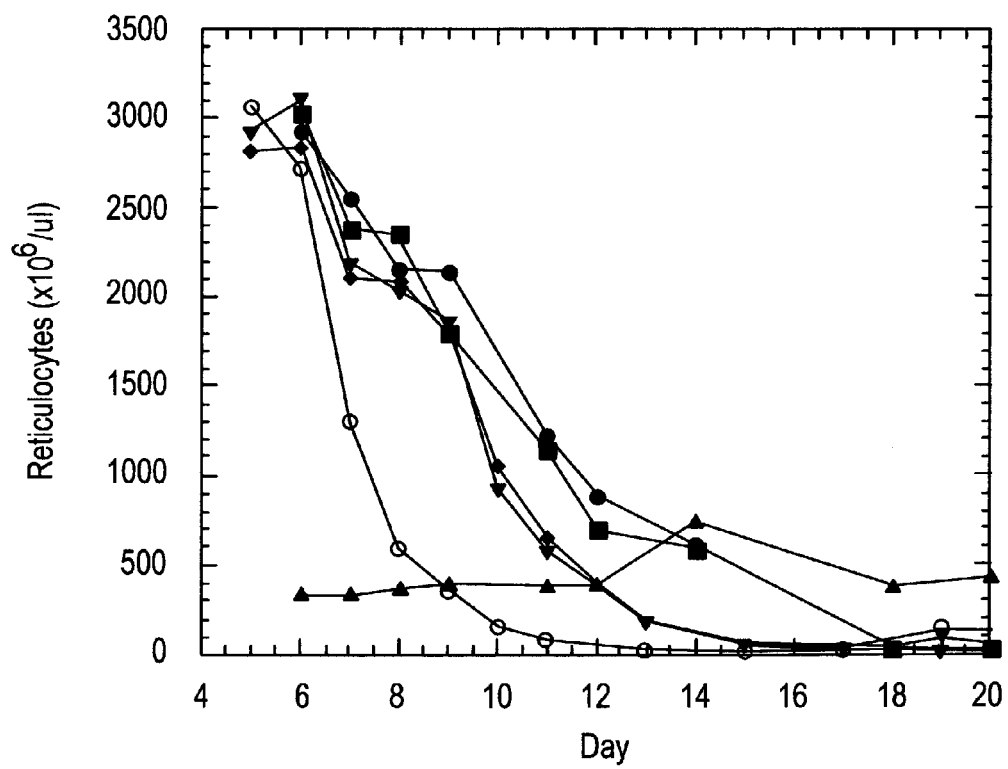
FIG. 5 is a graph depicting prolongation of elevated reticulocyte levels in response to treatment with various PEG:NESP conjugates relative to unmodified NESP. Single bolus injections of 100 μg/kg NESP (○), 20 kD linear mono-PEG:NESP (●), 5 kD linear mono-PEG:NESP (▼) and 5 kD linear di-PEG:NESP conjugates (♦) derived by reductive alkylation from aldehyde activated methoxy-PEG, a 20 kD branched mono-PEG:NESP (■) conjugate from NHS-ester activated PEG, and a saline control (▲). Absolute reticulocyte count is plotted vs. # days post-treatment.
Figure 6:
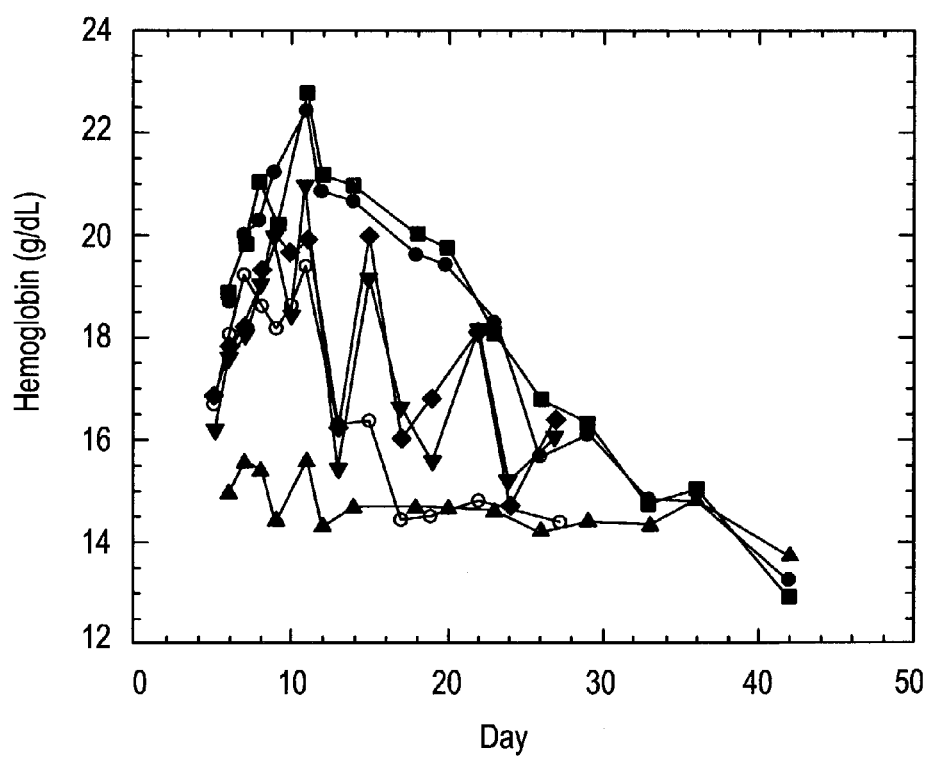
FIG. 6 is a graph depicting prolongation of elevated hemoglobin levels in response to treatment with various PEG:NESP conjugates relative to unmodified NESP. Single bolus injections of 100 μg/kg NESP (○), 20 kD linear mono-PEG:NESP (●), 5 kD linear mono-PEG:NESP (▼) and 5 kD linear di-PEG:NESP conjugates (♦) derived by reductive alkylation from aldehyde activated methoxy-PEG and a 20 kD branched mono-PEG:NESP conjugate (■) from NHS-ester activated PEG. HGB (g/dL) is plotted vs. # days post-treatment.
Figure 7:
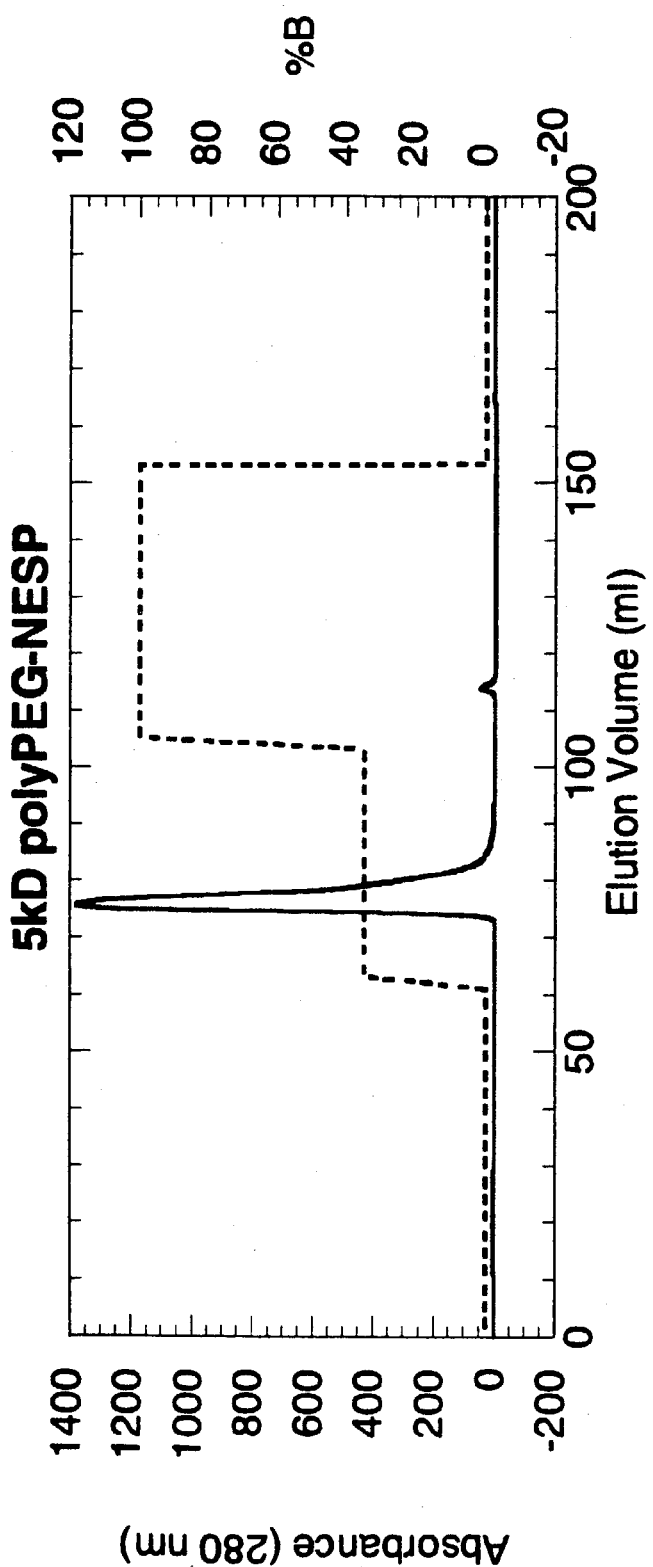
FIG. 7 depicts a Q Sepharose HP column chromatogram of the 5 kD poly-PEG:NESP conjugate. The column was a HiTrap Q Sepharose HP column which utilized a 50 mM NaCl to 200 mM NaCl linear gradient to elute the product.

The reaction with methoxy-PEG-NHS ester (Shearwater Polymers) was run with a NESP concentration of 4 mg/ml and a 5–7 fold molar excess of PEG in 50 mM Bicine buffer, pH 8. The reaction was stirred overnight at 4° C., then diluted 4-fold with 20 mM Tris, pH 7.2 and the pH adjusted to pH 7.4 with NaOH. The diluted reaction mixture was then loaded onto a 5 ml HiTrap Q Sepharose HP column (Pharmacia). The PEGylated NESP isoforms were resolved by elution with a 0–150 mM NaCl gradient in 20 mM Tris, pH 7.2 (see FIGS. 5–7).

These process schemes were employed for each of the 5 kD, 20 kD and 30 kD linear polymers as well as the 10 kD, 20 kD and 40 kD branched PEG-NHS esters. The various conjugates are listed in Table 1 below:

TABLE 1

| PEG polymer | Conjugation Chemistry | Degree of Substitution |
| --- | --- | --- |
| 5 kD linear | mPEG-NHS ester | mono/di-PEG |
| 20 kD linear | mPEG-NHS ester | mono-PEG |
| 20 kD linear | mPEG-NHS ester | di-PEG |
| 30 kD linear | mPEG-NHS ester | mono-PEG |
| 30 kD linear | mPEG-NHS ester | di-PEG |
| 5 kD linear | mPEG-aldehyde | mono-PEG |
| 5 kD linear | mPEG-aldehyde | di-PEG |
| 20 kD linear | mPEG-aldehyde | mono-PEG |
| 30 kD linear | mPEG-aldehyde | mono-PEG |
| 30 kD linear | mPEG-aldehyde | di-PEG |
| 10 kD branched | branched mPEG-NHS ester | mono/di-PEG |
| 20 kD branched | branched mPEG-NHS ester | mono-PEG |
| 40 kD branched | branched mPEG-NHS ester | mono-PEG |
| 20 kD branched | branched mPEG-aldehyde | mono-PEG |
| 40 kD branched | branched mPEG-aldehyde | mono-PEG |
| 5 kD linear | mPEG-hydrazide | high (>7 PEGs) |
| 5 kD linear | mPEG-hydrazide | low (1–5 PEGs) |
| 20 kD linear | mPEG-hydrazide | high (>7 PEGs) |
| 20 kD linear | mPEG-hydrazide | medium (~4–7 PEGs) |
| 20 kD linear | mPEG-hydrazide | low (1–5 PEGs) |

Figure 8:
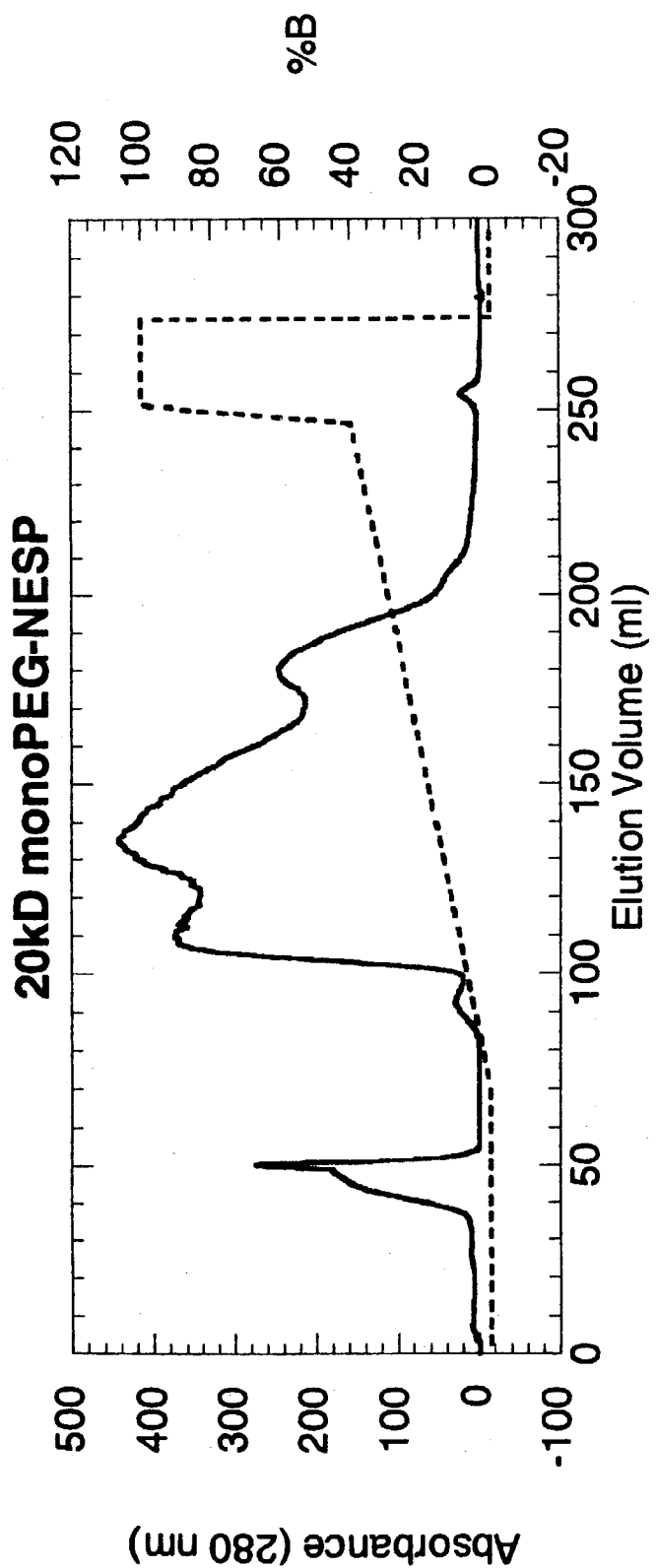
FIG. 8 depicts a Q Sepharose HP column chromatogram of the 20 kD mono-PEG:NESP conjugate. The column was a HiTrap Q Sepharose HP column which utilized a 50 mM NaCl to 200 mM NaCl linear gradient to elute the product.
Figure 9:
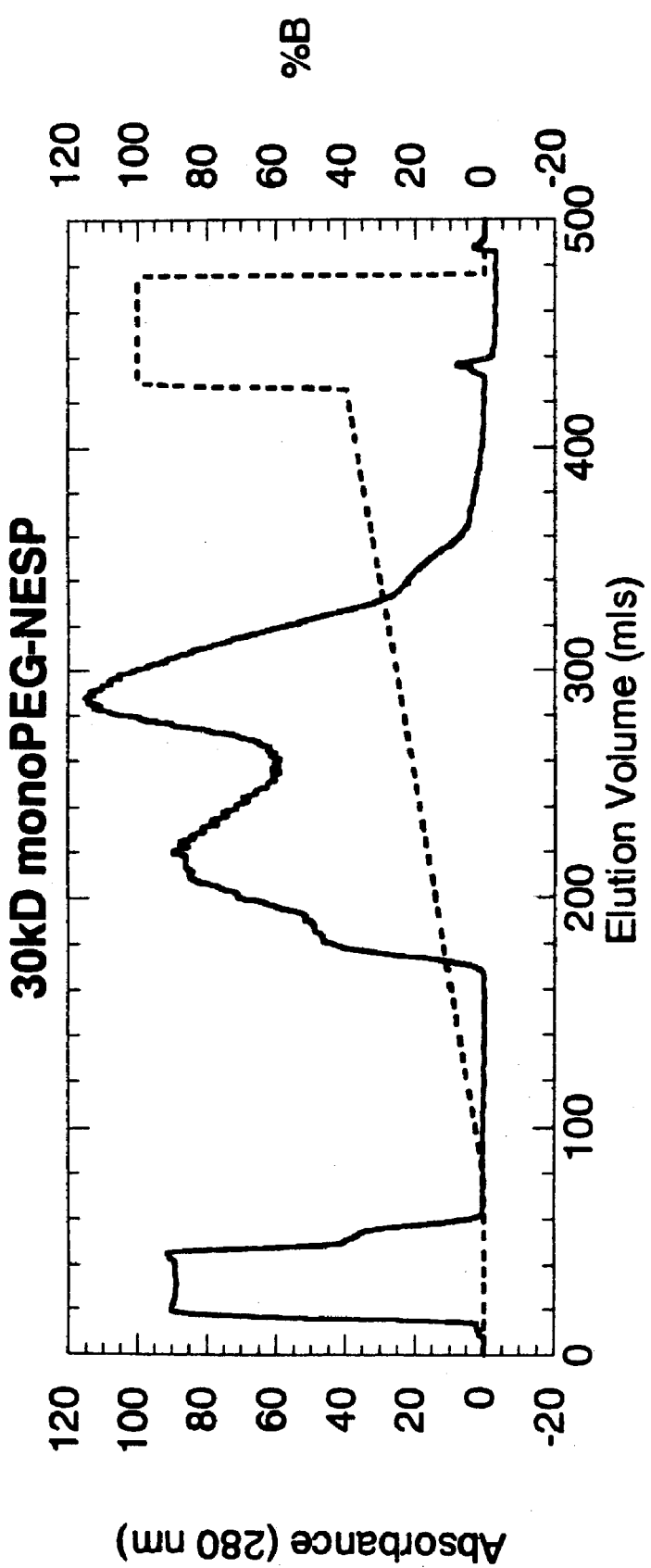
FIG. 9 depicts a Q Sepharose HP column chromatogram of the 30 kD mono-PEG:NESP conjugate. The column was a HiTrap Q Sepharose HP column which utilized a 50 mM NaCl to 200 mM NaCl linear gradient to elute the product.
Figure 10:
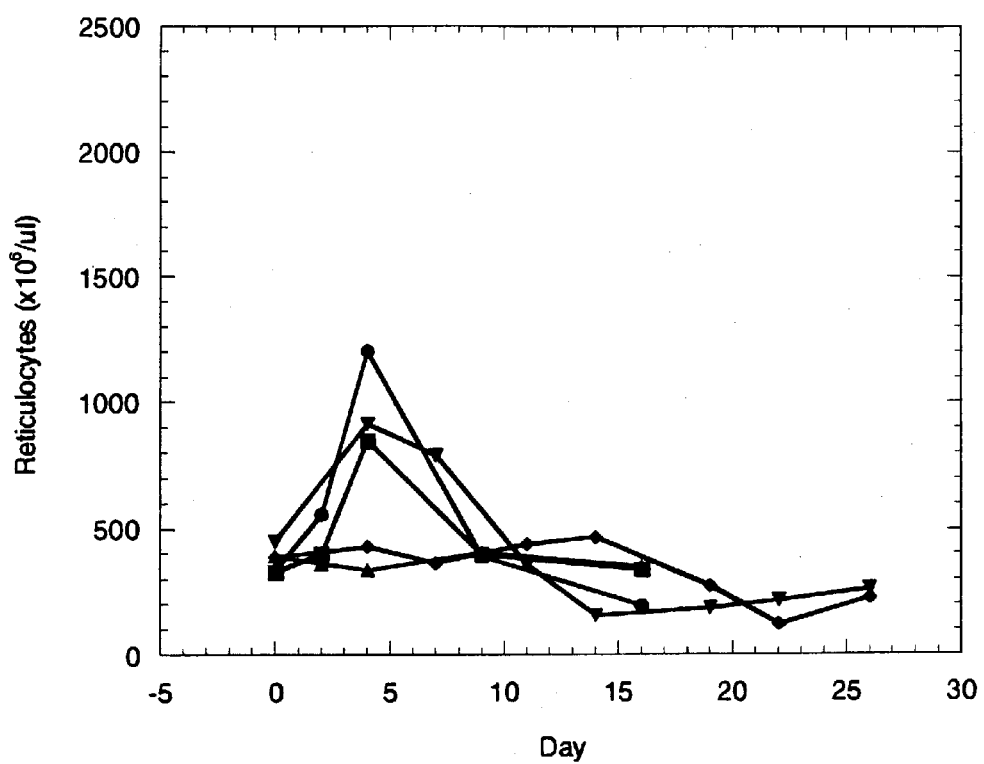
FIG. 10 is a graph depicting reticulocyte response of anemic mice after single bolus injections of 3 μg/kg 30 kD mono-PEG:NESP conjugate (▼), 3 μg/kg 20 kD mono-PEG:NESP conjugate (■), and 3 μg/kg 5 kD poly-PEG:NESP conjugate mixture (●). Absolute reticulocyte count is plotted vs. # days post-treatment.
Figure 11:
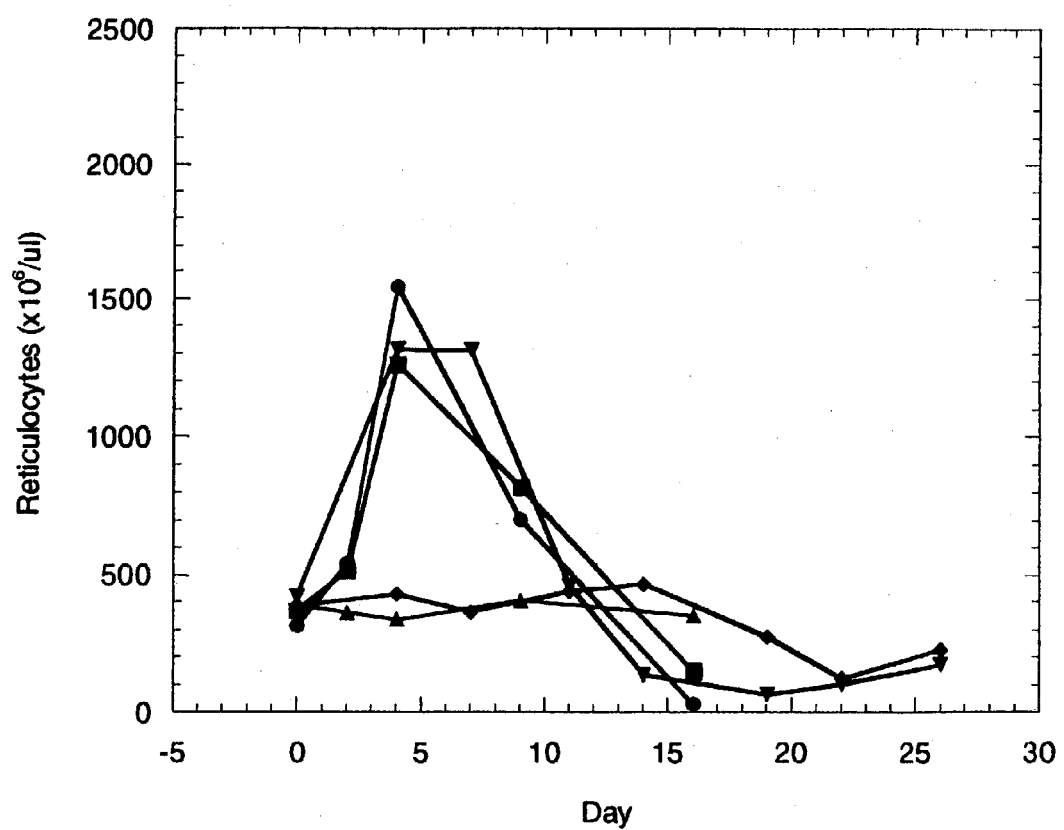
FIG. 11 is a graph depicting reticulocyte response of anemic mice after single bolus injections of 10 μg/kg 30 kD mono-PEG:NESP conjugate (▼), 10 μg/kg 20 kD mono-PEG:NESP conjugate (■), and 10 μg/kg 5 kD poly-PEG:NESP conjugate mixture (●). Absolute reticulocyte count is plotted vs. # days post-treatment.
Figure 12:
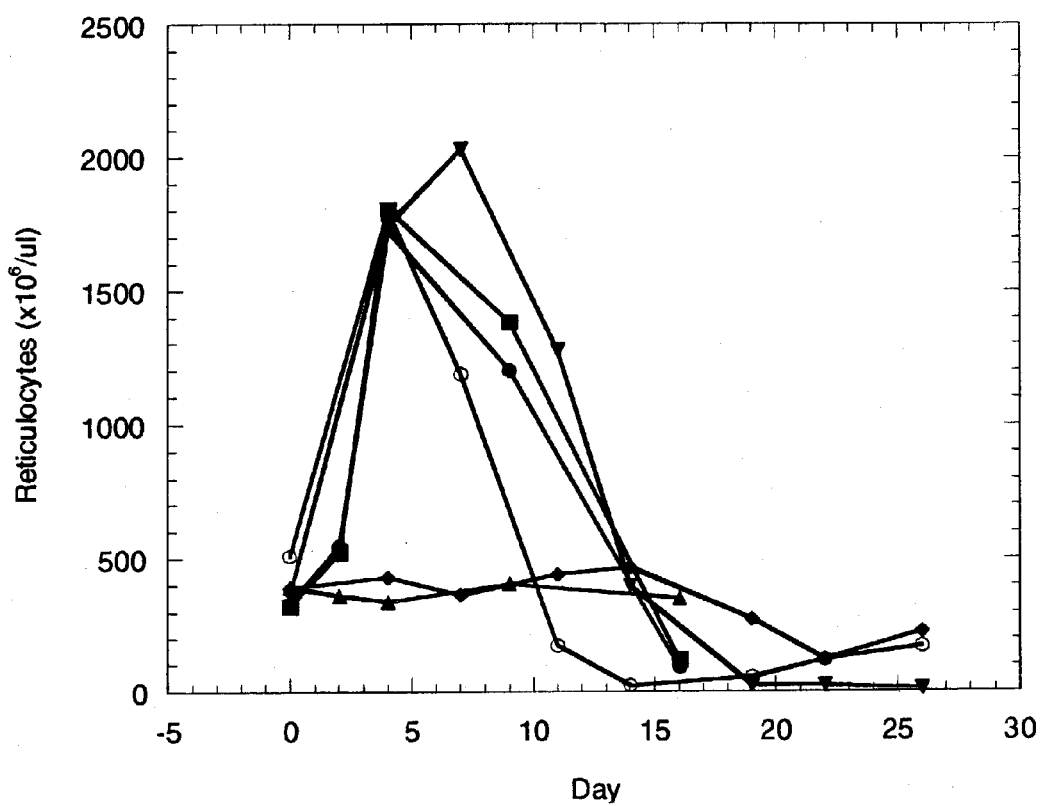
FIG. 12 is a graph depicting reticulocyte response of anemic mice after single bolus injections of 30 μg/kg 30 kD mono-PEG:NESP conjugate (▼), 30 μg/kg 20 kD mono-PEG:NESP conjugate (■), and 30 μg/kg 5 kD poly-PEG:NESP conjugate mixture (●) vs. 30 μg/kg unmodified NESP (○). Absolute reticulocyte count is plotted vs. # days post-treatment.
Figure 13:
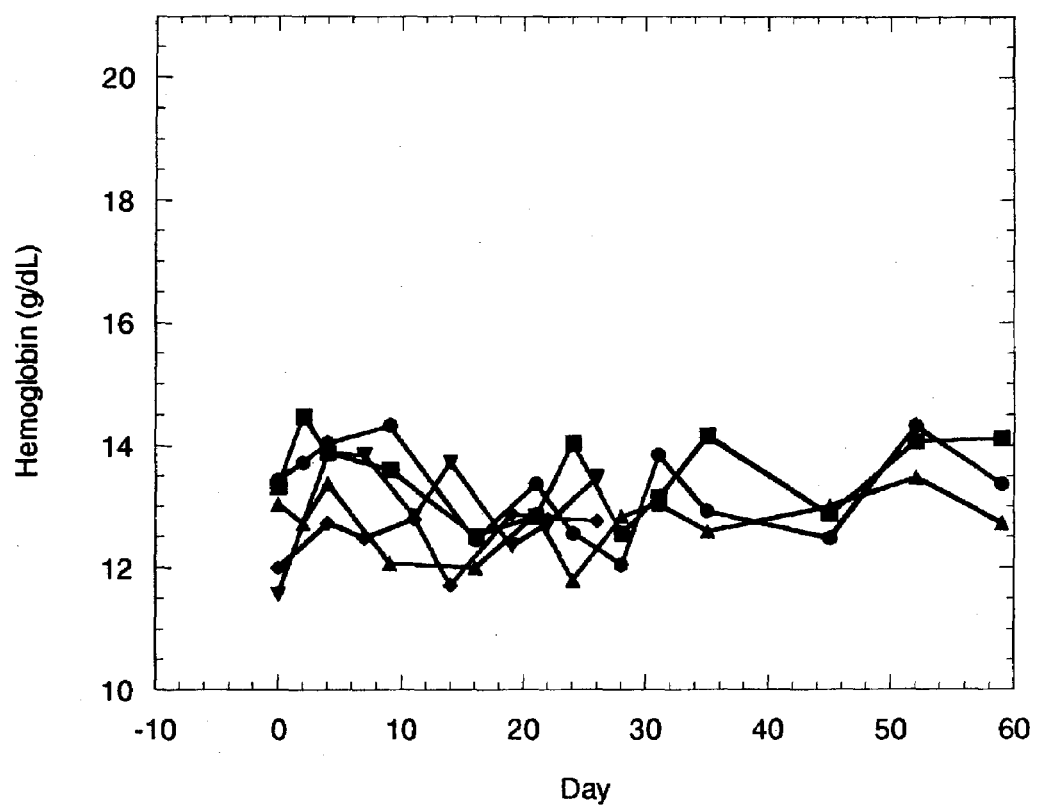
FIG. 13 is a graph depicting hemoglobin response of anemic mice after single bolus injections of 3 μg/kg 30 kD mono-PEG:NESP conjugate (▼), 3 μg/kg 20 kD mono-PEG:NESP conjugate (■), and 3 μg/kg 5 kD poly-PEG:NESP conjugate mixture (●). HGB (g/dL) is plotted vs. # days post-treatment.
Figure 14:
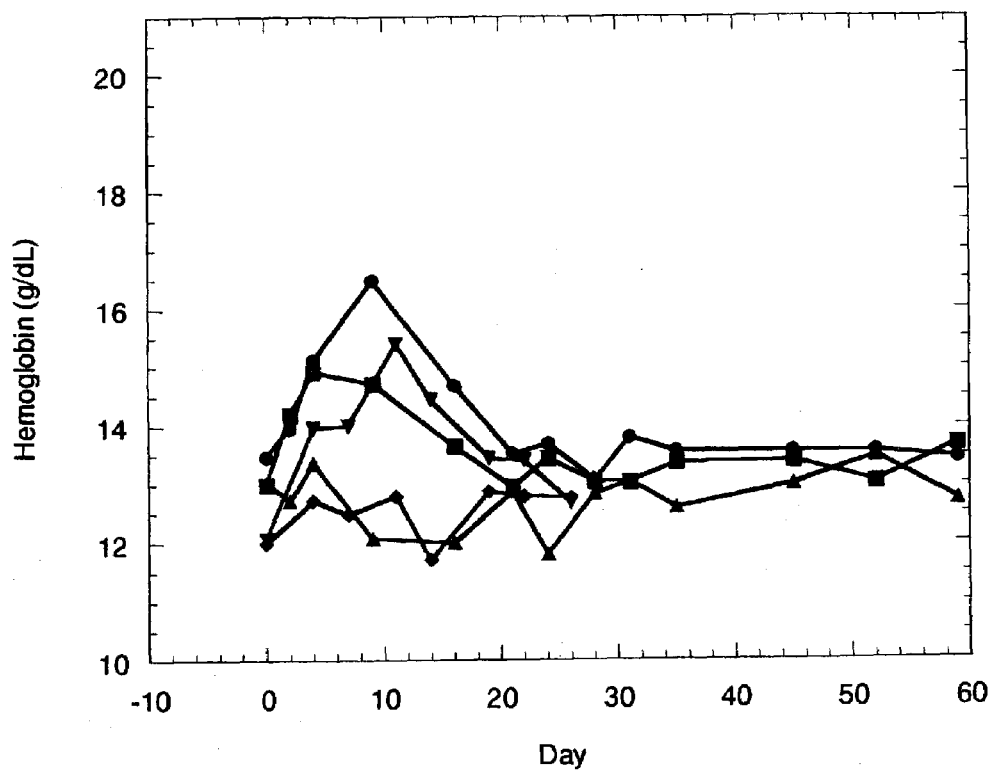
FIG. 14 is a graph depicting hemoglobin response of anemic mice after single bolus injections of 10 μg/kg 30 kD mono-PEG:NESP conjugate (▼), 10 μg/kg 20 kD mono-PEG:NESP conjugate (■), and 10 μg/kg 5 kD poly-PEG:NESP conjugate mixture (●). HGB (g/dL) is plotted vs. # days post-treatment.
Figure 15:
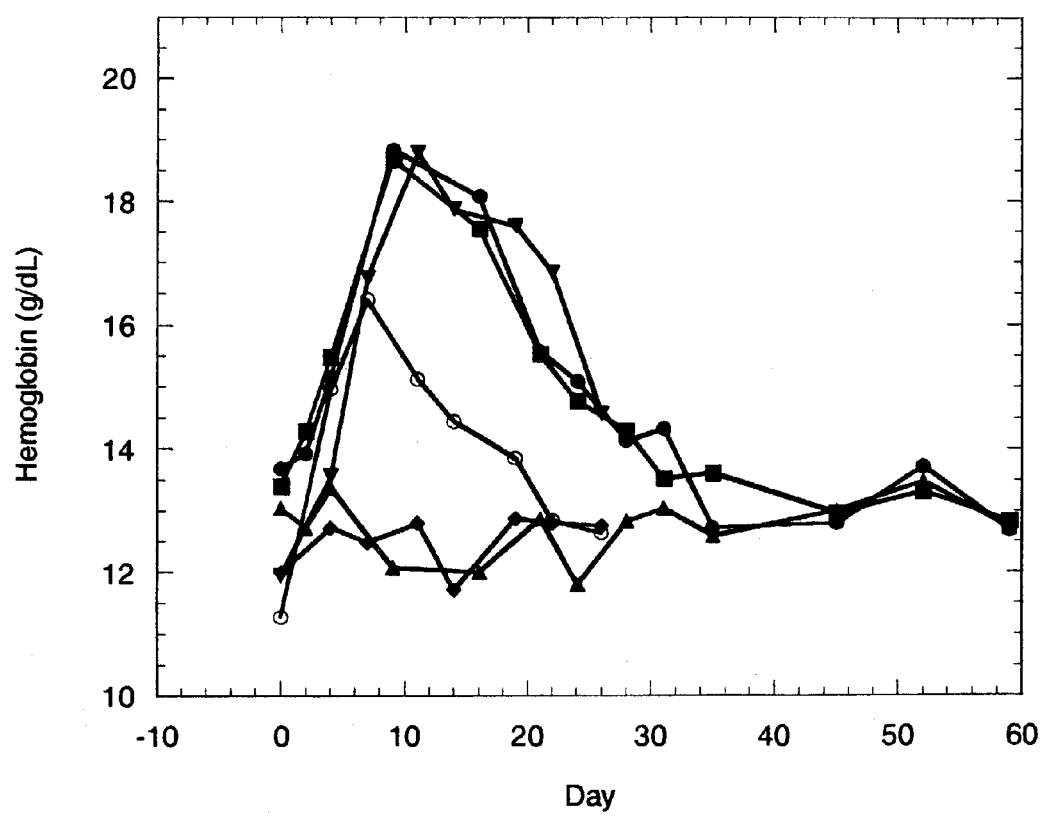
FIG. 15 is a graph depicting hemoglobin response of anemic mice after single bolus injections of 30 μg/kg 30 kD mono-PEG:NESP conjugate (▼), 30 μg/kg 20 kD mono-PEG:NESP conjugate (■), and 30 μg/kg 5 kD poly-PEG:NESP conjugate mixture (●) vs. 30 μg/kg unmodified NESP (○). HGB (g/dL) is plotted vs. # days post-treatment.
Figure 16:
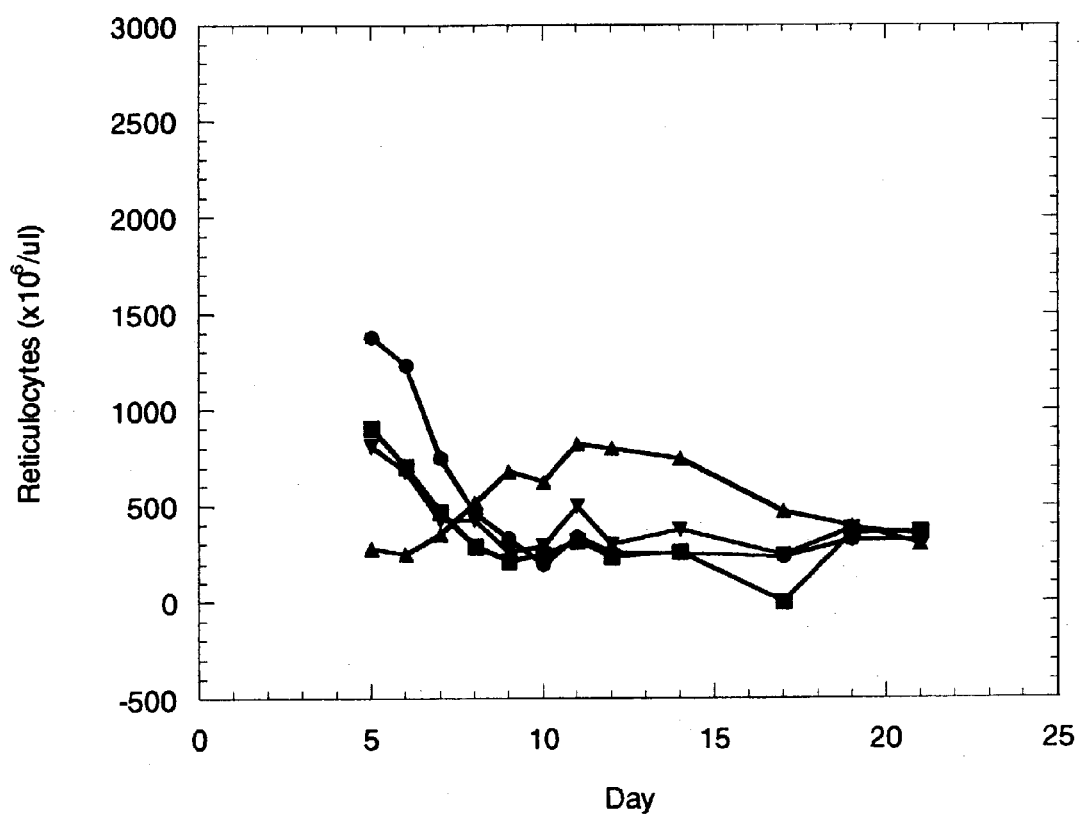
FIG. 16 is a graph depicting reticulocyte response of normal mice after single bolus injections of 3 μg/kg 30 kD mono-PEG:NESP conjugate (▼), 3 μg/kg 20 kD mono-PEG:NESP conjugate (■), and 3 μg/kg 5 kD poly-PEG:NESP conjugate mixture (●). Absolute reticulocyte count is plotted vs. # days post-treatment.
Figure 17:
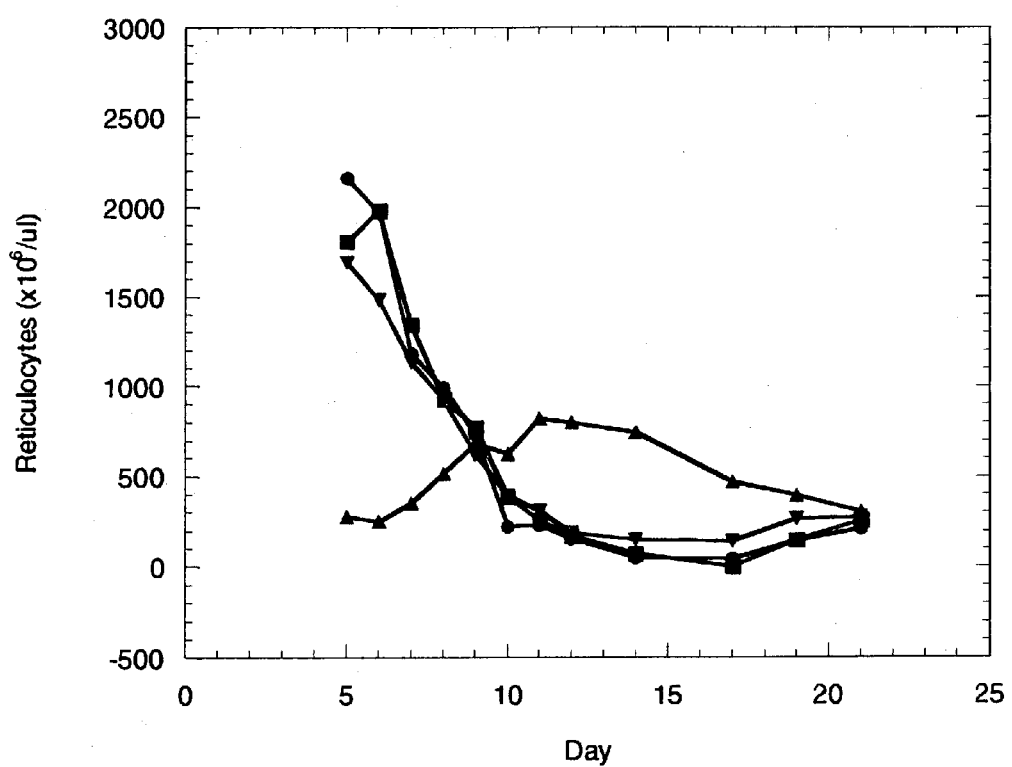
FIG. 17 is a graph depicting reticulocyte response of normal mice after single bolus injections of 10 μg/kg 30 kD mono-PEG:NESP conjugate (▼), 10 μg/kg 20 kD mono-PEG:NESP conjugate (■), and 10 μg/kg 5 kD poly-PEG:NESP conjugate mixture (●). Absolute reticulocyte count is plotted vs. # days post-treatment.
Figure 18:
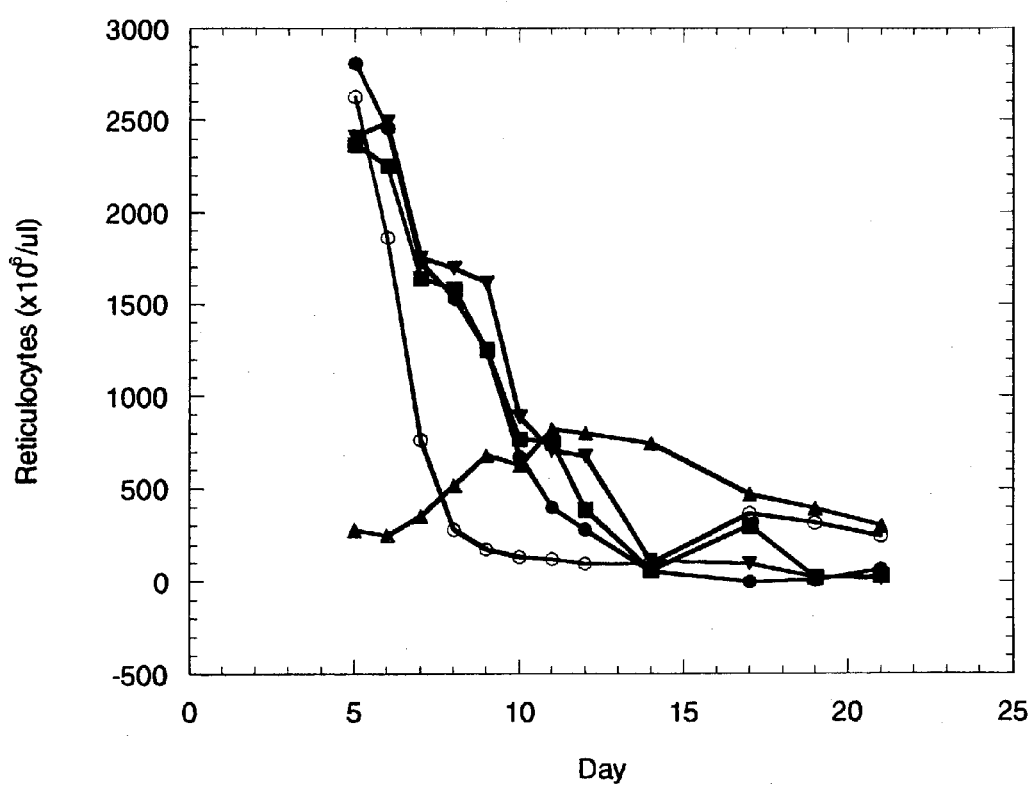
FIG. 18 is a graph depicting reticulocyte response of normal mice after single bolus injections of 30 μg/kg 30 kD mono-PEG:NESP conjugate (▼), 30 μg/kg 20 kD mono-PEG:NESP conjugate (■), and 30 μg/kg 5 kD poly-PEG:NESP conjugate mixture (●) vs. 30 μg/kg unmodified NESP (○). Absolute reticulocyte count is plotted vs. # days post-treatment.
Figure 19:
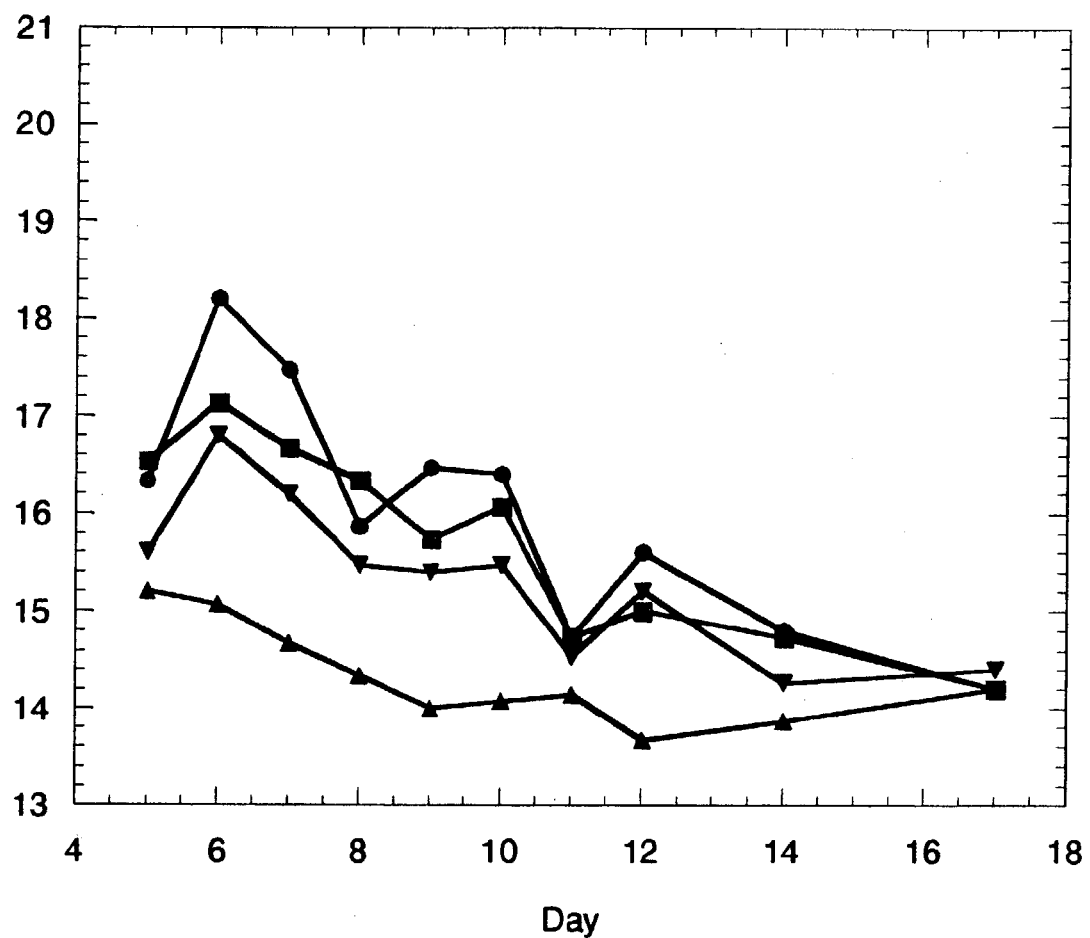
FIG. 19 is a graph depicting hemoglobin response of normal mice after single bolus injections of 3 μg/kg 30 kD mono-PEG:NESP conjugate (▼), 3 μg/kg 20 kD mono-PEG:NESP conjugate (■), and 3 μg/kg 5 kD poly-PEG:NESP conjugate mixture (●). HGB (g/dL) is plotted vs. # days post-treatment.
Figure 20:
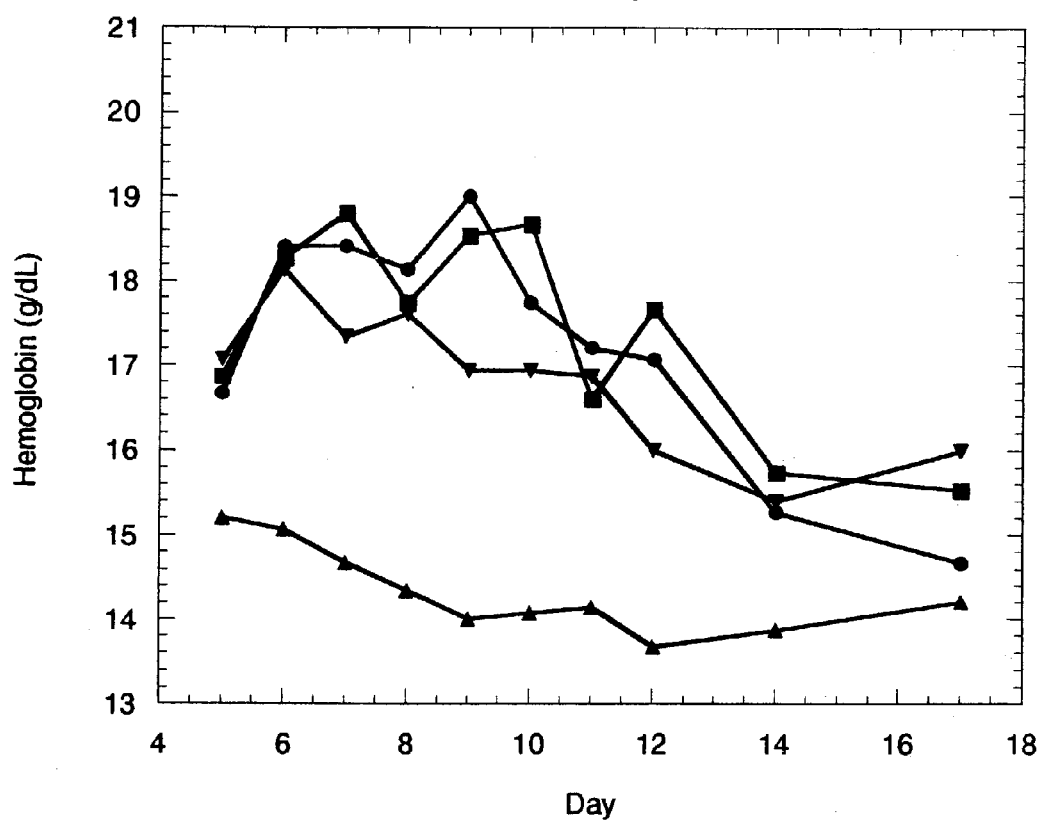
FIG. 20 is a graph depicting hemoglobin response of normal mice after single bolus injections of 10 μg/kg 30 kD mono-PEG:NESP conjugate (▼), 10 μg/kg 20 kD mono-PEG:NESP conjugate (■), and 10 μg/kg 5 kD poly-PEG:NESP conjugate mixture (●) HGB (g/dL) is plotted vs. # days post-treatment.
Figure 21:
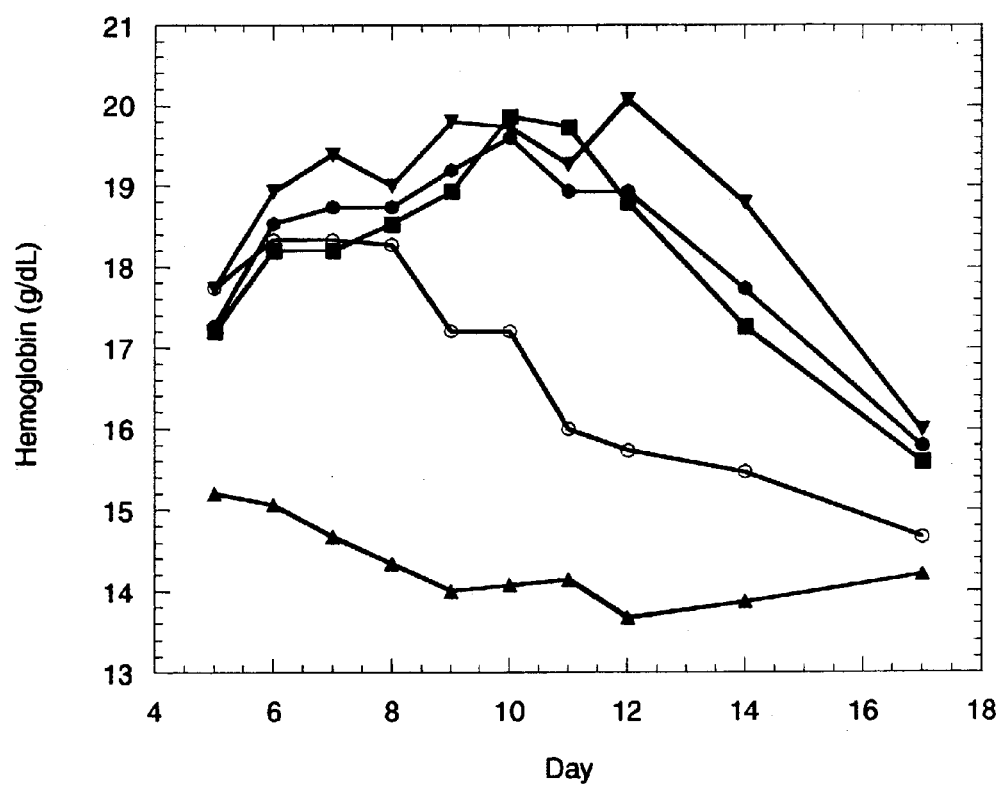
FIG. 21 is a graph depicting hemoglobin response of normal mice after single bolus injections of 30 μg/kg 30 kD monb-PEG:NESP conjugate (▼), 30 μg/kg 20 kD mono-PEG:NESP conjugate (■), and 30 μg/kg 5 kD poly-PEG:NESP conjugate mixture (●) vs. 30 μg/kg unmodified NESP (○). HGB (g/dL) is plotted vs. # days post-treatment.

Each purified isoform was then tested in a murine in vivo bioassay for prolonged erythropoietic activity as measured by changes in reticulocyte and hemoglobin determinations after single, subcutaneous bolus injections of 100 μg/kg in normal, female BDF 1 mice. Each mono-substituted PEG:NESP conjugate from the linear and branched polymer series showed significant and comparable prolongation of the erythropoietic effect (see FIGS. 8 and 9). The di-substituted PEG:NESP conjugates from the 20 kD and 30 kD PEG polymers were considerably less active, but unexpectedly, the 5 kD di-substituted PEG:NESP conjugate demonstrated an equivalent activity to the mono-substituted counterpart. All of the mono-substituted, branched PEG:NESP conjugates demonstrated prolonged activity comparable to the analogous mono-substituted linear PEG:NESP conjugates.

These examples thus demonstrate the enhanced duration of erythropoietic stimulation by a variety of PEG:NESP conjugates using single-dose, bolus injections in normal mouse models.

EXAMPLE 4

This example describes the efficacy of three PEG:NESP conjugates: 20 kD mono-PEG:NESP; the 5 kD poly-PEG:NESP mixture; and 30 kD mono-PEG:NESP, as examined at three different doses relative to a NESP control, in an anemic mouse model.

To induce an anemic condition, mice were pretreated with cis-platinin at 1 mg/kg/day for 3 days, followed by a 7 day rest period. After 3 ten day cycles, the mice were dosed with single, bolus injections of 30 μg/kg, 10 μg/kg or 3 μg/kg of the 20 kD mono-PEG:NESP, 30 kD mono-PEG:NESP or the 5 kD poly-PEG:NESP conjugates and compared to a NESP alone control at 30 μg/kg. Reticulocyte and hemoglobin levels were monitored as a function of time and in response to the single dose of each drug (see FIGS. 10–15).

These data demonstrate the unexpected advantages of an ~3 fold dose reduction and significant increases in erythropoietic half-life for the PEG:NESP conjugates relative to NESP alone, in that the results demonstrate a clear dose dependence for both the magnitude and duration of either the reticulocyte or hemoglobin response to the PEG:NESP conjugates. In some cases the 30 kD mono-PEG:NESP conjugate appears to modestly outperform the 5 kD poly-PEG:NESP conjugate, which modestly outperforms the 20 kD mono-PEG:NESP conjugate, suggesting that the 30 kD mono-PEG:NESP conjugate might be a preferred configuration.

EXAMPLE 5

In this example, three different PEG-NESP conjugates were evaluated in a normal mouse bioassay to compare and contrast their erythropoietic potential and duration. The three compounds tested were: 30 kD mono-PEG:NESP derived by acylation with the 30 kD PEG-NHS ester, the 20 kD mono-PEG:NESP derived by reductive alkylation with the 20 kD PEG-aldehyde and the 5 kD poly-PEG:NESP mixture derived by reductive alkylation with the 5 kD PEG-aldehyde. Each PEG:NESP conjugate was tested as a single bolus, subcutaneous dose at 30 μg/kg, 10 μg/kg or 3 μg/kg. Unmodified NESP was used as a control at 30 μg/kg in a single, bolus injection. The erythropoietic response and duration were monitored as a function of reticulocyte counts or hemoglobin concentration (see FIGS. 16–21) as a function of time. These data show that all three PEG:NESP forms are capable of inducing a strong erythropoietic response with significant dose reduction. Moreover, these PEG:NESP conjugates demonstrate a prolonged efficacy relative to the unmodified NESP.

Materials and Methods

The present NESP may be prepared according to the above incorporated-by-reference PCT Application No. US94/02957.

The conjugates prepared herein were also characterized using size exclusion chromatography (SEC) as an analytical tool. The SEC column was a Tosohaas TSK 3000 SW×1 (5 micron-7.8 mm×30 cm) which utilized 100 mM NaHPO$_4$, 10% ethanol, 150 mM NaCl, pH 6.9, to elute the products. A representative chromatograph is depicted in FIG. 22.

While the present invention has been described in terms of certain preferred embodiments, it is understood that variations and modifications will occur to those skilled in the art. Therefore, it is intended that the appended claims cover all such equivalent variations which come within the scope of the invention as claimed.

4. The method of claim 1 wherein said NESP has the amino acid sequence of SEQ ID NO:1.

5. The method of claim 1 wherein said polyethylene glycol has a molecular weight of between 2 kD and 100 kD.

6. The method of claim 5 wherein said preparation is administered once every four to six weeks.

7. The method of claim 1 wherein said polyethylene glycol has a molecular weight of between 5 kD and 30 kD.

8. The method of claim 7 wherein said preperation is administered at a dose in a range of 3 to 100 μg/kg.

The invetion claimed is:

1. A method of increasing hematocrit in a mammal comprising administering a therapeutically effective dose of a substantially homogenous preparation of a chemically modified hyperglycosylated Novel Erythropoietin Stimulating Protein (NESP) wherein said NESP is chemically modified with polyethylene glycol (PEGylated); and wherein said preparation is comprised of a mixed population of mono-PEGylated NESP and poly-PEGylated NESP and wherein at least 95% of the NESP molecules are PEGylated.

2. The method of claim 1 where said preparation is comprised of a mixed population of mono-PEGylated NESP and poly-PEGylated NESP.

3. The method of claim 1 where said preparation is comprised of at least 95% N-terminally mono-PEGylated NESP and at most 5% unPEGylated NESP.

9. A method of increaing hematocrit in a mammal comprising administering a therapeutically effective dose of a pharmaceutical composition comprising:

a. a substantially homogenous preparation of mono-PEGylated NESP, said mono-PEGylated NESP consisting of a polyethylene glycol moiety connected to a NESP moiety selectively at the N-terminus thereof;

(b) fewer than 5% non-PEGylated NESP molecules; and (c) a pharmaceutically acceptable diluent, adjuvant or carrier.

10. A method of increaing hematocrit in a mammal comprising administering a therapeutically effective dose of a pharmaceutical composition comprising:

a. substantially homogenous preparation of mono-PEGylated NESP, said mono-PEGylated NESP consisting of a polyethylene glycol moiety connected to a NESP moiety through aldehydes generated in NESP carbohydrates chains;

(b) fewer than 5% non-PEGylated NESP molecules; and (c) a pharmaceutically acceptable diluent, adjuvant or carrier.

11. A method of increaing hematocrit in a mammal comprising administering a therapeutically effective dose of a pharmaceutical composition comprising:

a. a substantially homogenous preparation of mono-PEGylated NESP, said mono-PEGylated NESP consisting of a polyethylene glycol moiety connected to a NESP moiety through methoxy-polyethylene glycol-N-hydroxysuccinimidyl ester chemistry;

(b) fewer than 5% non-PEGylated NESP molecules; and (c) a pharmaceutically acceptable diluent, adjuvant or carrier.

12. A method of increaing hematocrit in a mammal comprising administering a therapeutically effective dose of a pharmaceutical composition comprising:

a. substantially homogenous preparation of a chemically modified hyperglycosylated protein, PEGylated NESP, said PEGylated NESP comprising a mixed population of mono-PEGylated NESP and poly-PEGylated NESP;

(b) fewer than 5% non-PEGylated NESP molecules; and (c) a pharmaceutically acceptable diluent, adjuvant or carrier.

13. The method of any of claims 9, 10, 11, and 12 wherein said polyethylene glycol has a molecular weight of between 2 kD and 100 kD.

14. The method of any of claims 9, 10, 11, and 12 wherein said polyethylene glycol has a molecular weight of between 5 kDA and 30 kD.

15. The method of any of claims 9, 10, 11, and 12 wherein said preparation is administered once every four to six weeks.

16. The method of any of claims 9, 10, 11, and 12 wherein said preparation is administered at a dose in a range of 3 to 100 µg/kg.

* * * * *

UNITED STATES PATENT AND TRADEMARK OFFICE
CERTIFICATE OF CORRECTION

PATENT NO. : 7,262,166 B2
APPLICATION NO. : 10/409807
DATED : August 28, 2007
INVENTOR(S) : Kinstler et al.

It is certified that error appears in the above-identified patent and that said Letters Patent is hereby corrected as shown below:

Column 6, line 41, replace "(typically... amino" to read --(typically $\alpha$ or $\epsilon$ amino--.

Column 9, line 7, replace "petiodate" to read --periodate--.

Column 9, line 43, replace "dm" to read --cm--.

Column 13, line 62, replace "where" to read --wherein--.

Column 13, line 65, replace "where" to read --wherein--.

Column 14, line 52, replace misspelled word "increaing" to read --increasing--.

Column 14, line 63, replace misspelled word "increaing" to read --increasing--.

Column 15, line 3, replace "carbohydrates" to read --carbohydrate--.

Column 15, line 7, replace misspelled word "increaing" to read --increasing--.

Column 15, line 10, replace "a. a" to read --a.--.

Column 15, line 18, replace misspelled word "increaing" to read --increasing--.

Column 16, line 7, replace "claims 9, ..." to read --claims 1, 9 ...--.

Column 16, line 11, replace "claims 9, ..." to read --claims 1, 9 ...--.

Column 16, line 14, replace "claims 9, ..." to read --claims 1, 9 ...--.

UNITED STATES PATENT AND TRADEMARK OFFICE
CERTIFICATE OF CORRECTION

PATENT NO. : 7,262,166 B2
APPLICATION NO. : 10/409807
DATED : August 28, 2007
INVENTOR(S) : Kinstler et al.

It is certified that error appears in the above-identified patent and that said Letters Patent is hereby corrected as shown below:

Column 16, line 17, replace "claims 9, ..." to read --claims 1, 9 ...--.

Signed and Sealed this

Fifteenth Day of December, 2009

David J. Kappos
*Director of the United States Patent and Trademark Office*